US007642423B2

(12) United States Patent
Nicolet et al.

(10) Patent No.: US 7,642,423 B2
(45) Date of Patent: Jan. 5, 2010

(54) PEPPER PLANTS

(75) Inventors: Jean Louis Marie Edouard Nicolet, Sarrians (FR); Hermanus Everardus Johannes Koning, De Blaker (NL)

(73) Assignee: Syngenta Participations AG, Basel (CH)

( * ) Notice: Subject to any disclaimer, the term of this patent is extended or adjusted under 35 U.S.C. 154(b) by 312 days.

(21) Appl. No.: 10/918,067

(22) Filed: Aug. 13, 2004

(65) Prior Publication Data

US 2005/0055743 A1   Mar. 10, 2005

Related U.S. Application Data

(60) Provisional application No. 60/495,774, filed on Aug. 15, 2003.

(51) Int. Cl.
- A01H 5/00 (2006.01)
- A01H 5/10 (2006.01)
- C12N 15/82 (2006.01)

(52) U.S. Cl. .................... 800/317.1; 435/410
(58) Field of Classification Search ............... 800/317.1
See application file for complete search history.

(56) References Cited

U.S. PATENT DOCUMENTS

| 4,843,186 | A | 6/1989 | Nahum |
| 5,440,069 | A | 8/1995 | Czaplewski et al. |
| 5,763,742 | A | 6/1998 | Morrison et al. |
| 5,811,640 | A | 9/1998 | Grun et al. |
| 5,824,873 | A | 10/1998 | Grierson et al. |
| 5,945,580 | A | 8/1999 | Dunsmuir et al. |
| 6,498,287 | B2 | 12/2002 | Nash |

FOREIGN PATENT DOCUMENTS

| CA | 2315289 | 1/2002 |
| WO | WO 96/09755 | 4/1996 |
| WO | WO 01/84912 | 11/2001 |
| WO | WO 02/12450 | 2/2002 |
| WO | WO 02/33105 | 4/2002 |

OTHER PUBLICATIONS

Park Seed Co. Park Seed, Flower and vegetable catalog, 1991, p. 112.*
Ahmed et al, *Effects of different fruit maturity stages and storages conditions of chemical composition and market acceptability of fruit in different varieties of sweet pepper Capsicum and Eggplant Newsletter*, vol. 15 (1996) pp. 47-50.
Economic and Social Council for the United Nations (Jan. 11, 2002), UNECE Standard FFV-28 concerning the marketing and commercial quality control of sweet peppers moving in international trade between and to UNECE member countries. Document No. TRADE/WP.7/2001/9/Add.2.
Fallik et al, *A Unique Rapid Hot Water Treatment to Improve Storage Quality of Sweet Pepper Postharvest Biology and Technology*, vol. 15 (1999) pp. 25-32.
Ferrarese et al, *Differential ethylene-inducible expression of cellulose in pepper plants Plant Molecular Biology*, vol. 29 (1995) pp. 735-747.
Ghaouth et al, Use of Chitosan Coating to Reduce Water Loss and Maintain Quality of Cucumber and Bell Pepper Fruits *Journal of Food Processing and Preservation*, vol. 15 (1991) pp. 359-368.
González et al, Storage Quality of Bell Peppers Pretreated with Hot Water and Polyethylene Packaging *Journal of Food Quality*, vol. 22 (1999) pp. 287-299.
González, G. and Tiznado, M., *Postharvest Physiology of Bell Peppers Stored in Low Density Polyethylene Bags Lebensm.-Wiss. U.-Technol.* vol. 26 (1993) pp. 450-455.
Gross et al, Biochemical changes associated with the ripening of hot pepper fruit *Physiologia Plantarum*, vol. 66 (1986) pp. 31-36.
Hampshire et al, *Bell pepper texture measurement and degradation during cold storage* ASAE Paper No. 87-6005. (1987) 19 p.
Harpster et al, Characterization of a PCR Fragment Encoding 1-Aminocyclopropane-1-Carboxylate Synthase in Pepper (*Capsicum annum*) *Journal of Plant Physiology*, vol. 147 (1996) pp. 661-664.
Harpster et al, Isolation and characterization of a gene encoding endo-β-1,4-glucanase from pepper (*Capsicum annuum* L.) *Plant Molecular Biology*, vol. 33 (1997) pp. 47-59.
Hungarian patent application HU2001002964, 2003-270523, Antal Es Tarsa Bt (with translated abstract).
Jen, J.J. and Robinson, M. L., Pectolytic Enzymes in Sweet Bell Peppers (*Capsicum annuum* L.) *Journal of Food Science*, vol. 49 (1984) pp. 1085-1087.
Miller et al, Decay, Firmness and Color Development of Florida Bell Peppers Dipped in Chlorine and Imazalil, and Film Wrapped *Proceedings of the Florida State Horticultural Society*, vol. 96 (1983) pp. 347-350.
Poulos, J.M., Pepper breeding (*Capsicum spp*.): achievements, challenges and possibilities *Plant Breeding Abstracts*, vol. 64, No. 6 (1994) Abstract 6284, pp. 860.
Priel A., *Seeds—Intellectual Property; Which Gains Profits Fruit World International* Mar. 2004 (Sep. 10, 2004) pp. 164-167; with publisher confirmation.
Rapido sales brochure with translation; distributed Sep. 8, 2003.
Russo, V.M., *Delaying harvest improves bell pepper yield Hortscience*, vol. 31, No. 3 (1996) pp. 345-346.
Showalter, R.K., *Guidelines for Pepper Quality Improvement Proceedings of the Florida State Horticultural Society*, vol. 92 (1979) pp. 136-139.
United States Standards for Grades of Sweet Peppers (Jan. 3, 1989); U.S. Department of Agriculture.
Wang, C. Y., Effect of $CO_2$ Treatment on Storage and Shelf Life of Sweet Peppers *Journal of American Society of Horticulture Science*, vol. 102(6), (1977) pp. 808-812.

* cited by examiner

*Primary Examiner*—Anne Marie Grunberg
*Assistant Examiner*—Keith O. Robinson
(74) *Attorney, Agent, or Firm*—S. Matthew Edwards

(57) ABSTRACT

The present invention relates to novel plants, in particular to *Capsicum annuum* plants capable of producing fruits with extended storability after full coloring of the fruit, and to seeds and fruits of said plants. The present invention also relates to methods of making and using such plants and their fruits. In particular, fruits of plants of the present invention retain marketability over extended periods of time compared to presently available peppers.

10 Claims, No Drawings

PEPPER PLANTS

CROSS-REFERENCE TO RELATED APPLICATIONS

This application claims the benefit of U.S. Provisional Application No. 60/495,774, filed Aug. 15, 2003. The above application is incorporated herein by reference.

FIELD OF THE INVENTION

The present invention relates to novel plants, in particular to pepper plants capable of producing fruits with extended storability, and to seeds and fruits of said plants. The present invention also relates to methods of making and using such plants and their fruits.

BACKGROUND OF THE INVENTION

Peppers are an important crop worldwide with an estimated commercial value of about 500 million dollars a year. Peppers are Solanaceas from the genus *Capsicum*, which includes the species *Capsicum annuum* and *Capsicum frutescens*. Commercial peppers are diploids with n=12 chromosomes. Peppers are cultivated and used around the world as sweet peppers such as the bell pepper; or as pungent chili peppers, jalapeno peppers, and TABASCO® peppers; or as a source of dried powders of various colors such as paprika. The types of cultivated peppers can be differentiated by pungency, fruit shape, color and size (see for example U.S. Pat. No. 6,498,287).

Pepper fruits, also commonly referred to as "peppers", are highly perishable. They are prone to water loss and shriveling, which renders them unappealing to customers. Pepper crops produce peaks of fruits that are mature around the same time and have to be harvested quickly to avoid losses. This leads to waves of product, followed by periods of low supply. In order too address this problem and bring flexibility in the supply chain, substantial efforts have been made to improve the quality of pepper fruits during post-harvest storage. Treatments involving hot water and polyethylene packing (Gonzalez-Aguilar et al (1999) Journal of Food Quality 22: 287-299), application of $CO_2$ (Wang (1977) J. Amer. Soc. Hort. Sci. 102: 808-812) or other chemicals such as chlorine and Imazalil (Miller et al. (1983) Proc. Fla. State Hort. Soc. 96: 345-350) or chitosan (El Ghaouth et al. (1991) Journal of Food Processing and Preservation 15: 359-368), have been described. However, these treatments require substantial investments and increase costs of production. Moreover, some of them promote of fungal growth or undesired off-flavor production (El Ghaouth et al. (1991) Journal of Food Processing and Preservation 15: 359-368).

Attempts to increase post-harvest shelf-life of pepper fruits have also been made by genetic engineering approaches. For example, U.S. Pat. No. 5,945,580 reports the transformation of *Capsicum annuum* with DNA sequences of a hemi-cellulase gene. Reduction of hemi-cellulase activity in fruits of transformed plants was measured, leading to a moderate increase in the proportion of acceptable fruits after post-harvest storage at 4° C. However, the commercial viability of this approach has not been reported.

An alternative strategy has concentrated on delaying fruit ripening, whereby unripe fruits are usually harvested and let ripen post harvest. For example, U.S. Pat. No. 4,843,186 discloses tomatoes comprising the native tomato Rin gene and their delayed ripening. However, maturation of pepper fruits is a slow process and post-harvest ripening of pepper fruits results in wilted, low-quality fruits. Delaying fruit ripening in pepper is therefore not a preferred strategy.

There is therefore an unmet need in the pepper trade to reduce peaks in production and to favor a constant supply of fresh products, while keeping production costs low. There is also an unmet need for improved pepper plants and for alternative and improved storage methods for pepper fruits.

SUMMARY OF THE INVENTION

The present invention addresses the need for more constant supply of pepper fruits and to provide flexibility in the pepper business chain. To solve this problem, the present invention provides novel *Capsicum* plants, preferably *Capsicum annuum* plants, capable of producing fruits, which remain marketable over extended periods of time beyond that of presently available pepper fruits, in particular presently available commercial pepper fruits. In particular, the *Capsicum* plants of the present invention are capable of producing fruits, which remain marketable over extended periods of time beyond that of presently available commercial pepper fruits, when the fruits are not harvested, but kept on the plant. In one embodiment, fruits of a pepper plant of the present invention are still marketable about 3 weeks after full coloring of said fruit, when said fruits are kept on the plant. In one embodiment, fruits of a pepper plant of the present invention are still marketable about 4 weeks, in one embodiment about 5 weeks, in one embodiment about 6 weeks, after full coloring of said fruit, when said fruits are kept on the plant. In another embodiment, the fruits of the plants of the present invention are capable of retaining one or more of the following characteristics such as e.g. firmness, resistance to climacteric spots, resistance to wilting, brightness, over an extended period of time beyond that of presently available commercial pepper fruits. Accordingly, in one embodiment, fruits of a pepper plant of the present invention remain firm about 3 weeks after full coloring of said fruit, when said fruits are kept on the plant. In one embodiment, fruits of a pepper plant of the present invention remain firm about 4 weeks, in one embodiment about 5 weeks, in one embodiment about 6 weeks, after full coloring of said fruit, when said fruits are kept on the plant. In another embodiment, fruits of a pepper plant of the present invention do not wilt about 3 weeks after full coloring of said fruit, when said fruits are kept on the plant. In one embodiment, fruits of a pepper plant of the present invention are do not wilt about 4 weeks, in one embodiment about 5 weeks, in one embodiment about 6 weeks, after full coloring of said fruit, when said fruits are kept on the plant. In another embodiment, fruits of a plant of the present invention show not more than 5 yellow spots or less about 3 weeks after full coloring, when said fruits are kept on the plant. In one embodiment, fruits of a pepper plant of the present invention show not more than 5 yellow spots or less about 4 weeks, in one embodiment about 5 weeks, in one embodiment about 6 weeks, after full coloring of said fruit, when said fruits are kept on the plant. In another embodiment, fruits of a plant of the present invention remain bright about 3 weeks after full coloring, when said fruits are kept on the plant. In one embodiment, fruits of a pepper plant of the present invention remain bright about 4 weeks, in one embodiment about 5 weeks, in one embodiment about 6 weeks after, full coloring of said fruit, when said fruits are kept on the plant.

In another embodiment, pepper fruits of the present invention exhibit delayed degradation compared to presently available commercial pepper fruits.

In another embodiment, a plant of the present invention is an inbred, a hybrid or a dihaploid. In another embodiment, a plant of the present invention is male sterile. In one embodiment, a plant of the present invention has commercially acceptable agronomic characteristics.

Accordingly, the present invention provides novel pepper plants capable of producing fruit exhibiting extended storability beyond that of presently available commercial pepper fruits, preferably extended storability on the plant. In one embodiment, fruits of pepper plants of the present invention exhibit extended storability on the plant after full coloring when compared to presently existing pepper. Therefore, plants of the present invention comprise a trait conferring extended storability as described herein to the fruits of said plants. In one embodiment, a trait of extendable storability according to the present invention is obtainable from a plant of hybrid Y1194, representative seed of which is deposited under Accession no. NCIMB 41187. In one embodiment, a trait of extendable storability according to the present invention is obtainable from a plant of ZORO.27.42.7:DH1004, representative seed of which is deposited under Accession no. NCIMB 41241.

The present invention further provides the use of trait according to the instant invention to confer extended storability on the plant to the fruit of a *Capsicum annum* plant lacking said trait.

The present invention also provides methods of making and using pepper plants of the present invention and their fruits, such as methods of producing pepper plants according to the present invention and seeds thereof, or methods of producing pepper fruits according to the present invention, methods of storing pepper fruits and methods of extending the harvest time of a pepper fruit.

Plants of the present invention are particularly advantageous in that they allow for a longer harvest period and for a lower harvest frequency of the crop, while maintaining high fruit quality and avoiding losses. Mature fruits can be stored on the plant and the harvest of fruits grown from plants of the present invention can be delayed by several weeks. Thus, the present invention offers the possibility for the grower to harvest less often a higher fruit quantity per plant. A better planning of the harvest, better efficiency of the harvest and more ripe fruits per harvest is reached while keeping the same fruit quality. The present invention also allows for better planning of labor for harvest, grading and packing of the product, and for better planning for sales and delivery of the product, thereby substantially reducing losses in the business chains and thus production costs.

The instant invention thus further provides methods of making a harvest decision, and methods of increasing the returns of a pepper crop.

DEFINITIONS

Marketable: fit to be offered for sale in a market, wanted by purchasers. When referring to pepper fruits, marketability may be assessed by judging a fruit based on criteria that appeal to consumers, such as an acceptable appearance. Marketability may also be assessed by one or more characteristics, such as firmness of the fruit, the presence or absence of climacteric spots, wilting of the fruit or brightness.

Storability: when referred to a fruit, ability to be kept or maintained for a period of time under certain conditions while remaining marketable.

Storability "on the plant": refers to the ability of a fruit to be kept on the plant, i.e. not harvested, for a period of time while remaining marketable. In this case, the fruit is stored on the plant.

Storability "post-harvest": refers to as the ability of a fruit to be kept after harvest for a period of time while remaining marketable. This is also referred to as post-harvest storage. Post-harvest storage includes storage in the different stages of the business chain leading to the consumer and including storage by the consumer prior to consumption.

Full coloring: when a fruit reaches its mature color on about 90% of its surface.

Firmness: not yielding readily to touch or pressure, solidly composed, compact. Firmness may for example also be defined as when a pepper fruit is not soft, shriveled, limp or pliable, although it may yield to slight pressure (e.g. US Standards for Grades of Sweet Peppers, USDA/AMS, Fruit and Vegetable Division, Fresh Products Branch).

Climacteric spots: yellow spots appearing after ripening on the shoulder of the fruit as a result of a degradation of the fruit structure.

Wilting: when referring to a fruit, loosing freshness, drooping. Wilting generally results in loss of smoothness of the fruit, and is typically accompanied with shrinking of the fruit.

Brightness: characteristic of emitting or reflecting much light, shining.

Trait: characteristic or phenotype, for example a resistance to a disease. In the context of the present invention a trait is for example extended storability of a fruit as described herein. A trait may be inherited in a dominant or recessive manner, or in a partial or incomplete-dominant manner. A trait may be monogenic or polygenic, or may also result from the interaction of one or more genes with the environment.

Resistance: characteristic or phenotype of a plant to exhibit no symptoms or insignificant symptoms of a condition, for example a disease.

Monogenic: determined by a single locus.

Polygenic: determined by more than one locus.

Dominant: results in a complete phenotypic manifestation at heterozygous or homozygous state.

Recessive: manifests itself only when present at homozygous state.

Partial or incomplete-dominance: when present at the heterozygous stage determines a phenotype that is intermediate to that of the homozygous stage or when the trait is absent.

Locus: region on a chromosome, which comprises a gene contributing to a trait.

Genetic linkage: association of characters in inheritance due to location of genes in proximity on the same chromosome. Measured by percent recombination between loci (centi-Morgan, cM).

Isogenic: plants, which are genetically identical, except that they may differ by the presence or absence of a gene, a locus conferring a trait or heterologous DNA sequence.

Marker assisted selection: refers to the process of selecting a desired trait or desired traits in a plant or plants by detecting one or more nucleic acids from the plant, where the nucleic acid is associated with the desired trait.

Dihaploid: doubling of haploid (single chromosome) status of the genome (e.g. through anther culture or microspore culture) giving a complete homozygous plant.

"Tester" plant: plant used to characterize genetically a trait in a plant to be tested. Typically, the plant to be tested is crossed with a "tester" plant and the segregation ratio of the trait in the progeny of the cross is scored.

Gene: Unit of inheritance. Genes are located at fixed loci in chromosomes and can exist in a series of alternative forms called alleles.

Allele: One of a pair or series of forms of a gene, which are alternative in inheritance because they are situated at the same locus in homologous chromosomes.

Homozygous: Having like alleles at one or more corresponding loci on homologous chromosomes.

Heterozygous: Having unlike alleles at one or more corresponding loci on homologous chromosomes.

DETAILED DESCRIPTION OF THE INVENTION

The present invention addresses the need for a more constant supply of pepper fruits in the business chain and for alternative to methods of storing pepper fruits. Accordingly, the present invention provides novel pepper plants capable of producing fruits, which remain marketable over extended periods of time beyond that of presently available peppers, in particular presently available commercial pepper fruits. In particular, fruits of the plants of the present invention retain their marketability when kept on the plant for an extended period of time beyond that of presently available commercial pepper fruits. The present invention therefore discloses pepper plants comprising a trait that confers extended storability to a fruit on said plant.

The present invention allows for delaying harvest of the fruit, depending on the needs of the market, on the availability of post-harvest storage and on appropriate transport to the consumer. Use of post-harvest storage is therefore avoided or substantially reduced. The plants of the present invention and their fruits, and methods of making and using such plants and fruits, are described in further details below.

Pepper seeds are generally germinated in a nursery or glasshouse. The germinated plantlets are then transplanted to grow full-size plants. After fruit setting, green fruits grow on the plant to reach mature size. Fruits at mature size then turn color to reach their final color (e.g. red, orange or yellow). The development of the final color of the fruit is generally correlated with degradation of chlorophyll (Wang (1977) J. Amer. Soc. Hort. Sci. 102: 808-812).

The time period from seeds sowing to first fruit setting and later first fruit coloring depends on the growth conditions. Generally, under warm and humid conditions, growth and development of the plant is faster, while cold conditions result in a slower growth. Differences between varieties or types of pepper are also observed with some varieties or types growing and producing mature fruits faster than other. In general, the time span from seeds sowing to first fruit setting varies between approximately 7 and 10 weeks, while the time span between first fruit setting and first fruit with full coloring varies between approximately 6 and 8 week. In glasshouse in the Netherlands, a pepper plant typically bears about 60 to 70 fruits over a period of 30 weeks. Pepper plants are grown in the open field or in glasshouse, with a harvest period of approximately 2 months in open fields, and of approximately 7 months in glasshouse.

Once harvested, the fruits are usually brought to a packing station, where they may be stored briefly (around one day), preferably at cool temperature (e.g. at about 8-14° C.). The fruits are then transported to a retailer, for example a supermarket, generally in a cooled truck. The transport may take 2-3 days. In the supermarket, the fruits are placed on the shelves for about 1-2 days at a temperature of about 17-18° C. It takes therefore about 5-10 days from the field to consumers, who expect to be able to keep fruits with good appearance for a few more days.

The pepper plants of the present invention are capable of producing fruits exhibiting extended storability on the plant after full coloring of the fruit. Such fruits are capable of maintaining marketable quality for extended periods of time when fruits are kept on the plant and not harvested when compared to currently available peppers.

In one embodiment, the present invention discloses a plant capable of producing a fruit, which is still marketable about 5 weeks after full coloring when said fruit is kept on the plant. In one embodiment, the present invention discloses a plant capable of producing a fruit, which is still marketable about 6 weeks after full coloring when said fruit is kept on the plant. In one embodiment, the present invention discloses a plant capable of producing a fruit, which is still marketable about 7 weeks, in one embodiment about 8 weeks, in one embodiment about 9 weeks, in one embodiment about 10 weeks, or in one embodiment about 11 weeks, after full coloring when said fruit is kept on the plant. In one embodiment, the present invention discloses a plant capable of producing a fruit, which is marketable up to about 11 weeks after full coloring when said fruit is kept on the plant.

In one embodiment, about 100% of the fruits of a plant of the present invention are still marketable about 3 weeks after full coloring when kept on the plant. This means that fruits of the present invention are marketable from about the time of full coloring until about three weeks thereafter. In one embodiment, the fruits of the present invention are still marketable about 4 weeks after full coloring, in one embodiment about 5 weeks after full coloring, in one embodiment about 6 weeks after full coloring, when kept on the plant. This means that such fruits are marketable from about the time of full coloring until about 4 weeks, about 5 weeks or about 6 weeks thereafter. In one embodiment of the invention a plant is provided producing fruits about 100% of which are marketable between about 3 weeks and up to about 6 weeks after full coloring, when said fruits are kept on the plant.

In one embodiment, about 90% of the fruits of a plant of the instant invention are still marketable about 4 weeks after full coloring, in one embodiment about 5 weeks, in one embodiment about 6 weeks, in one embodiment about 7 weeks, after full coloring when kept on the plant. In one embodiment of the invention a plant is provided producing fruits about 90% of which are marketable between about 4 weeks and up to 7 weeks after full coloring, when said fruits are kept on the plant.

In one embodiment of the invention a plant is provided producing fruits about 80% of which are marketable between about 4 weeks and up to 9 weeks after full coloring, when said fruits are kept on the plant. In one embodiment of the invention a plant is provided producing fruits about 85% of which are marketable about 9 weeks after full coloring, when said fruits are kept on the plant.

In one embodiment of the invention a plant is provided producing fruits about 60% of which are marketable between about 4 weeks and up to 9 weeks after full coloring, when said fruits are kept on the plant. In one embodiment of the invention a plant is provided producing fruits at least about 60% of which are marketable about 4 weeks full coloring, when said fruits are kept on the plant.

In one embodiment, about 50% of the fruits of a plant of the instant invention are still marketable about 4 weeks after full coloring, in one embodiment about 5 weeks after full coloring, in one embodiment about 6 weeks after full coloring, in one embodiment about 8 weeks after full coloring when kept on the plant.

In one embodiment, about 20% of the fruits of a plant of the present invention are marketable about 10 weeks after full coloring when kept on the plant.

In one embodiment, the plants of the present invention are grown in glasshouse, for example under the conditions as described in the examples below.

In contrast, currently available pepper fruits generally start losing marketability after 2 weeks after full coloring under the same conditions, and currently available pepper plants typically bear less than about 40% marketable fruits after 4 weeks after full coloring, about 0% marketable fruits after 5 weeks after full coloring, under these conditions. The present invention therefore allows for a substantially longer harvest period than that of currently available pepper fruits, without incurring fruit losses. In one embodiment, the harvest period for a pepper fruit of a plant of the instant invention is extended by about one week, in one embodiment by about two weeks, as compared with fruits of currently available pepper plants. Accordingly, in one embodiment, pepper fruits of the present invention remain marketable longer that fruits of a standard pepper plant, especially a commercially available pepper plant such as, for example the hybrid Sprinter, when the fruits are kept on the plant. In one embodiment, plants of the present invention are capable of harbouring about 100% marketable fruits for one more week than plants of a standard pepper plant, but especially a commercially available pepper plant such as, for example the hybrid Sprinter, when the fruits are kept on the plant. In one embodiment, plants of the present invention are capable of harbouring about 100% marketable fruits for two more weeks, in one embodiment three more weeks, in one embodiment, four more weeks, than plants of as compared to a standard pepper plant, but especially a commercially available pepper plant such as, for example the hybrid Sprinter, when the fruits are kept on the plant. In one embodiment, plants of the present invention are capable of harbouring about 90% marketable fruits for one more week than plants of a standard pepper plant, but especially a commercially available pepper plant such as, for example the hybrid Sprinter, when the fruits are kept on the plant. In one embodiment, plants of the present invention are capable of harbouring about 90% marketable fruits for two more weeks, in one embodiment three more weeks, in one embodiment, four more weeks, than plants of a standard pepper plant, but especially a commercially available pepper plant such as, for example the hybrid Sprinter, when the fruits are kept on the plant.

In one embodiment, the marketability of the fruits is judged by the appearance of the fruits. Particularly, marketability of pepper fruits is assessed by one or more characteristics, such as firmness of the fruit, the presence or absence of climacteric spots, wilting of the fruit or brightness. In one embodiment, the above marketability criteria of the pepper fruits are determined on plants grown in glasshouses, for example under the conditions set forth in the examples below.

Accordingly, the present invention also discloses methods of preserving the marketability of a pepper fruit on a plant over an extended period of time or extending the marketability of the fruits of a pepper plant comprising introducing a trait of extended storability according to the present invention into a plant lacking said trait.

In one embodiment, fruits of a pepper plant of the present invention are capable of remaining firm over an extended period of time when kept on the plant. In one embodiment, fruits of a pepper plant of the present invention show enhanced firmness over fruits of a standard pepper plant, but especially a commercially available pepper plant such as, for example hybrid Sprinter, when the fruits are kept on the plant.

In one embodiment, essentially all fruits of a plant of the present invention retain their firmness about 3 weeks after full coloring when kept on the plant. In one embodiment, essentially all fruits of a plant of the present invention retain their firmness about 4 weeks, in one embodiment about 5 weeks, in one embodiment about 6 weeks after full coloring when kept on the plant. In contrast, currently available pepper fruits generally start losing firmness after 2 weeks after full coloring to become unacceptably soft within 4 to 5 weeks after full coloring under the same conditions.

Accordingly, in on embodiment, pepper fruits of the present invention remain firm longer that fruits of a standard pepper plant, but especially a commercially available pepper plant such as, for example the hybrid Sprinter, when the fruits are kept on the plant. In one embodiment, plants of the present invention are capable of harbouring about 100% fruits that remain firm for about one more week than plants of standard hybrid Sprinter when the fruits are kept on the plant. In one embodiment, plants of the present invention are capable of harbouring about 100% fruits that remain firm for about two more weeks, in one embodiment about three more weeks, in one embodiment about four more weeks than plants of standard hybrid Sprinter when the fruits are kept on the plant.

The firmness of pepper fruits is determined by hand with finger pressure or using a firmness tester. Different scales are used to evaluate the firmness of pepper fruits and are described in detail in the examples below.

In one embodiment, the firmness of a pepper fruits is determined using a scale of 0-9 as disclosed in the examples below, and a fruit of a pepper plant according to the present invention with a firmness rated at 5 at the time of full coloring remains rated at 5 for the periods of time disclosed above. In another embodiment, fruits with a firmness rated at a different level at the time of full coloring on the 0-9 scale above, for example at level 4 or 6, remain rated at their rating at full coloring for the periods of time disclosed above.

In one embodiment, the firmness of pepper fruits is determined on plants grown in glasshouses, for example under the conditions set forth in the examples below.

Accordingly, the present invention also discloses methods of maintaining the firmness of a pepper fruit on a plant over an extended period of time comprising introducing a trait of extended storability according to the present invention into a plant lacking said trait.

In another embodiment, fruits of a pepper plant of the present invention exhibit extended resistance to wilting when kept on the plant. In one embodiment, fruits of a pepper plant of the present invention exhibit enhanced resistance to wilting when kept on the plant as compared to a standard pepper plant, but especially a commercially available pepper plant such as, for example the hybrid Sprinter In one embodiment, essentially all fruit of a plant according to the present invention remain smooth and are considered not wilted about 3 weeks after full coloring when kept on the plant.

In another embodiment, essentially all fruit of the present invention remain smooth and are considered not wilted about 4 weeks after full coloring, in one embodiment about 5 weeks after full coloring, in one embodiment about 6 weeks after full coloring when kept on the plant.

In contrast, currently available pepper fruits wilt after 2 weeks after full coloring when kept on the plant under standard greenhouse conditions, and almost all such fruits are wilted after 4 to 5 weeks on the plant after full coloring when kept on the plant.

Accordingly, in another embodiment, pepper fruits of the present invention are resistant to wilting longer that fruits of a standard pepper plant, but especially a commercially available pepper plant such as, for example the hybrid Sprinter, when the fruits are kept on the plant. In one embodiment, plants of the present invention are capable of harbouring about 100% fruits resistant to wilting for about one more week than plants of standard hybrid Sprinter when the fruits are kept on the plant. In one embodiment, plants of the present invention are capable of harbouring about 100% fruits resistant to wilting for about two more weeks, in one embodiment about three more weeks, in one embodiment about four more weeks than plants of standard hybrid Sprinter when the fruits are kept on the plant.

In one embodiment, wilting is determined according to a scale of 1-5 based on the approximate surface of a fruit affected by wilting as described in the examples below.

In one embodiment, fruits that are not wilted score at level 5 in the scale of 1-5 for wilting. In one embodiment, essentially no fruit of the present invention scores at level 4 or less in the scale for the periods of time set forth above. In another embodiment, about 40% of fruits of a plant according to the present invention score at level 4 or less on said scale about 8 weeks after full coloring when kept on the plant.

In one embodiment, the resistance to wilting of pepper fruits is determined on plants grown in glasshouses, for example under the conditions set forth in the examples below.

Accordingly, the present invention also discloses methods of delaying wilting or maintaining the smoothness of a pepper fruit when kept on a plant over an extended period of time comprising introducing a trait of extended storability according to the present invention into a plant lacking said trait.

Wilting is generally a result of dehydration of the fruit. Accordingly, in one embodiment, the present invention discloses pepper plants capable of producing fruits with extended resistance to dehydration. To measure dehydration, fruits are typically detached from the plant and weighted. Average weight losses are determined over time after full coloring.

In another embodiment, fruits of a pepper plant of the present invention exhibit resistance to climacteric spot or yellow spots over an extended period of time when kept on the plant. In one embodiment, a fruit is considered acceptable if is shows not more than 5 yellow spots or less. In one embodiment, the size of an acceptable spot is about 2 mm or less. In one embodiment, about 3 weeks after full coloring essentially no fruit on a plant according to the present invention shows more than 5 yellow spots when kept on the plant. In another embodiment, essentially no fruit on a plant according to the present invention shows more than 5 yellow spots about 4 weeks after full coloring, in one embodiment about 5 weeks after full coloring, in one embodiment about 6 weeks after full coloring, in one embodiment about 8 weeks after full coloring when kept on the plant.

In contrast, fruits of currently available pepper plants already show large amounts of climacteric spots 2 weeks after full coloring when kept on the plant under the same conditions.

Accordingly, in another embodiment, pepper fruits of the present invention are resistant to climacteric degradation longer that fruits of a standard pepper plant, but especially a commercially available pepper plant such as, for example the hybrid Sprinter, when the fruits are kept on the plant. In one embodiment, pepper fruits of the present invention exhibit enhanced resistance to climacteric degradation as compared to fruits of a standard pepper plant, but especially a commercially available pepper plant such as, for example hybrid Sprinter, when the fruits are kept on the plant. In one embodiment, plants of the present invention are capable of harbouring about 100% fruits resistant to climacteric degradation for about one more week than plants of standard hybrid Sprinter when the fruits are kept on the plant. In one embodiment, plants of the present invention are capable of harbouring about 100% fruits resistant to climacteric degradation for about two more weeks, in one embodiment about three more weeks, in one embodiment about four more weeks, in one embodiment about 8 more weeks than plants of standard hybrid Sprinter when the fruits are kept on the plant.

In one embodiment, the resistance to climacteric degradation of pepper fruits is determined on plants grown in glasshouses, for example under the conditions set forth in the examples below.

Accordingly, the present invention also discloses methods of extending resistance to yellow spots of a pepper fruit on a plant comprising introducing a trait of extended storability according to the present invention into a plant lacking said trait.

In another embodiment, fruits of a pepper plant of the present invention retain their brightness over an extended period of time when kept on the plant.

In one embodiment, about 3 weeks after full coloring essentially no fruit of a plant of the present invention kept on the plant scores level 2 or less in a scale of 0-5 for brightness, as set forth in the examples below. In one embodiment, essentially no fruit of the present invention scores at level 2 or less in the scale about 4 weeks after full coloring, in one embodiment about 5 weeks after full coloring, in one embodiment about 6 weeks after full coloring when kept on the plant. In another embodiment, about 40% of fruits on a plant according to the present invention score at level 2 or less on said scale about 8 weeks after full coloring when kept on the plant.

In contrast, substantial amounts of fruits of currently available pepper plants loose brightness within 2 weeks after full coloring when kept on the plant under the same conditions. Accordingly, in another embodiment, pepper fruits of the present invention remain bright longer that fruits of a standard pepper plant, but especially a commercially available pepper plant such as, for example the hybrid Sprinter, when the fruits are kept on the plant. In one embodiment, pepper fruits of the present invention exhibit enhanced brightness as compared to fruits of a standard pepper plant, but especially a commercially available pepper plant such as, for example, hybrid Sprinter, when the fruits are kept on the plant. In one embodiment, plants of the present invention are capable of harbouring about 100% fruits that remain bright for one more week than plants of standard hybrid Sprinter when the fruits are kept on the plant. In one embodiment, plants of the present invention are capable of harbouring about 100% fruits that remain bright for two more weeks, in one embodiment three more weeks, in one embodiment, four more weeks than plants of standard hybrid Sprinter when the fruits are kept on the plant.

In one embodiment, the brightness of pepper fruits is determined on plants grown in glasshouses, for example under the conditions set forth in the examples below. In one embodiment, glasshouse conditions are standard Dutch glasshouse conditions. Accordingly, the present invention also discloses methods of maintaining the brightness of a pepper fruit on a plant over an extended period of time comprising introducing a trait of extended storability according to the present invention into a plant lacking said trait.

In another embodiment, pepper fruits of the instant invention have a thick wall compared to other presently available peppers. The thickness of the wall is measured at the thinnest part of the wall of a fruit, which has been cut across. Fruits of plants of the present invention have a wall with a thickness of about 6 mm to about 8 mm, in one embodiment of about 6.5 mm to about 7.5 mm.

In another embodiment, the fruits of the plants of the present invention do not show delayed ripening. Fruits of plants of the present invention mature within time frames comparable to those of control plants, although slight differences may be observed depending for example on the growth conditions or on the genetic background of the plants examined. In particular, pepper plants of the instant invention set fruit and get full coloring around the same time as standard pepper plants. Absence of delayed fruit ripening is of advantage, as it does not delay the harvest of the first mature fruits.

In another embodiment, fruits of a pepper plant of the present invention exhibit outstanding post-harvest storability. In one embodiment, pepper fruits of the present invention remain marketable for about 16 to about 24 days post-harvest, in one embodiment for about 18 to about 22 days post-harvest, when stored at a temperature of about 16 to about 18° C.

In another embodiment, a pepper plant of the present invention is capable of producing fruits exhibiting one or more of the characteristics described. In one embodiment, a pepper plant of the present invention is capable of producing fruits exhibiting a combination of one or more of the characteristics of enhanced firmness, enhanced resistance to wilting, enhanced resistance to climacteric degradation and enhanced brightness. Accordingly, in one embodiment, a fruit of the instant invention exhibits enhanced firmness and enhanced resistance to wilting as described herein. In another embodiment, a fruit of the instant invention exhibits enhanced firmness and enhanced resistance to climacteric degradation as described herein. In another embodiment, a fruit of the instant invention exhibits enhanced firmness and enhanced brightness as described herein. In another embodiment, a fruit of the instant invention exhibits enhanced resistance to wilting and enhanced resistance to climacteric degradation as described herein. In another embodiment, a fruit of the instant invention exhibits enhanced resistance to wilting and enhanced brightness as described herein. In another embodiment, a fruit of the instant invention exhibits enhanced resistance to climacteric degradation and enhanced brightness as described herein.

In another embodiment, a fruit of the instant invention exhibits enhanced firmness, enhanced resistance to wilting and enhanced resistance to climacteric degradation as described herein. In another embodiment, a fruit of the instant invention exhibits enhanced firmness, enhanced resistance to wilting and enhanced brightness as described herein. In another embodiment, a fruit of the instant invention exhibits enhanced firmness, enhanced resistance to climacteric degradation and enhanced brightness as described herein. In another embodiment, a fruit of the instant invention exhibits enhanced resistance to wilting and enhanced resistance to climacteric degradation and enhanced brightness as described herein.

In another embodiment, a fruit of the instant invention exhibits enhanced firmness, enhanced resistance to wilting, enhanced resistance to climacteric degradation and enhanced brightness as described herein.

The characteristics of fruits of the present invention described above were measured under glasshouse conditions. However, pepper plants can be grown under other conditions, such as for example in open fields under various conditions. The person skilled in the art understands that different growth conditions may lead to variations in the periods of time for extended storability. For example, hot and dry conditions would generally shorten the duration of such periods, while cold weather and weaker sunlight would generally extend the duration of such periods. Under such varying conditions, the fruits of the present invention also exhibit superior characteristics compared to presently available peppers.

The period of time, for which a pepper fruit remains marketable, also depends on the genetic background of a pepper plant, in which the trait of the instant invention is present or has been introduced into. For example, the extension of the period of storability is generally longer in plants producing fruits with more firmness, while it is generally less pronounced in plants producing fruits with less firmness. In such varying genetic backgrounds, pepper fruits comprising the trait of the present invention exhibit superior characteristics compared to fruits of pepper plants of comparable background not comprising the trait of the present invention.

In one embodiment, the storability of a fruit of a pepper plant comprising a trait the present invention is extended when compared to that of a fruit of a standard pepper plant used as a control. In one embodiment, a standard pepper plant is a commercially available pepper variety. In one embodiment, the commercially available pepper variety is Sprinter. Accordingly, in one embodiment, the characteristics of the fruits of pepper plants of the present invention are measured and compared to standard hybrid Sprinter (Enza Zaden, Enkhuizen, The Netherlands). However, other similar pepper plants can be used as suitable standards in the measurements described herein, such as for example Express (a red hybrid of Enza Zaden), Pronto (a red hybrid of Syngenta Seeds), Fiesta (a yellow hybrid of Enza Zaden), Derby (de Ruiter, The Netherlands) or Ferrari (Enza Zaden, The Netherlands). In one embodiment, the storability of a fruit of a pepper plant comprising a, trait the present invention is extended when compared to that of a pepper plant not comprising said trait. In another embodiment, the storability of a pepper fruit of the present invention is extended when compared to a pepper plant isogenic to said plant, but not comprising said trait.

Characteristics of pepper fruits are measured using various tests, as for example disclosed herein. In one embodiment, measurements are carried out on individual fruits and averages are calculated. Standard deviations and confidence intervals (e.g. Chi Square) are calculated when appropriate. Other statistical tools well known in the art are also used when needed. Data for fruits on the plant are typically recorded at weekly intervals after full coloring of the fruits. Post-harvest data are typically recorded every day post-harvest.

The characteristics of the pepper fruits of the instant invention have been determined by the methods described in the examples. However, alternative methods known and accepted in the art may also be used to demonstrate the superior characteristics compared to presently available peppers. The skilled person also knows how to measure other characteristics of a pepper fruit. For example, the quality of a pepper fruit is determined following the 1-9 scale of according to Gonzalez-Aguilar et al (1999) Journal of Food Quality 22: 287-299. The respiration rate of a pepper fruit is measured, for example by measuring $CO_2$ and $O_2$ concentrations. For example, $CO_2$ and $O_2$ concentrations are determined over time after full coloring of the fruit, for example following protocols described in Gonzalez and Tiznado (1993) Lebensm.-Wiss. u.-Technol. 26: 450-455. Ethylene production of the fruits is measured over time after full coloring of the fruits, for example using the protocol as described in (Wang (1977) J. Amer. Soc. Hort. Sci. 102: 808-812). Soluble solids, titrable acidity, or pH are measured over time after full coloring of a pepper fruit. Protocols as described in Gonzalez and Tiznado (1993) Lebensm.-Wiss. u.-Technol. 26: 450-455 are for example used. Enzymatic activities in the pepper fruits are measured after full coloring. For example, the activities of pectolytic enzymes such as polygalacturonase or pectinesterase are determined, for example according to the methods described in Jen and Robinson (1984) Journal of Food Science 49: 1085-1087. These measurements may also be used to demonstrate the superior quality of the pepper fruits of the invention.

Based on the description of the present invention, for example the test for marketability and other characteristics described herein, the skilled person is able to recognize a pepper plant comprising the trait of the present invention under various growth conditions. Accordingly, the present invention also further discloses a method of identifying a pepper plant of the instant invention comprising growing a pepper plant until a fruit of said plant reaches full coloring, determining the marketability of said fruit over time, wherein said fruit exhibits extended marketability according to the present invention. In one embodiment, the firmness, resistance to wilting, resistance to climacteric degradation or brightness of said fruit is determined over time as described herein.

Seed of pepper hybrid Y1194, a representative *Capsicum* plant according to the instant invention was deposited under the Budapest treaty with NCIMB, Aberdeen AB2 1RY, Scotland, UK under accession number NCIMB 41187 on Jul. 31, 2003. Hybrid Y1194 is heterozygous for the trait of the instant invention and is also heterozygous for a genetic male sterility. Hybrid Y1194 is further described in the examples below.

Pepper hybrid Y1301 also produced fruits with extended storability on the plant beyond that of presently available commercial pepper fruits, although the extension of the period of storability is less pronounced for Y1301 than for Y1194.

Seed of pepper line ZORO.27.42.7:DH1004, a representative *Capsicum* plant according to the instant invention was deposited under the Budapest treaty with NCIMB, Aberdeen AB2 1RY, Scotland, UK under accession number NCIMB 41241 on Aug. 12, 2004. Line ZORO.27.42.7:DH1004 is a dihaploid line and is further described in the examples below.

In one embodiment, the trait of the present invention is obtainable from pepper hybrid Y1194, deposited under accession no. NCIMB 41187, or from a progeny or ancestor of said line comprising said trait. In another embodiment, the trait of the present invention is obtained or derived from pepper hybrid Y1194, deposited under accession no. NCIMB 41187, or from a progeny or ancestor of said line comprising said trait.

In one embodiment, the trait of the present invention is obtainable from pepper line ZORO.27.42.7:DH1004 or from a progeny or ancestor of said line comprising said trait. In another embodiment, the trait of the present invention is obtained or derived from pepper line ZORO.27.42.7:DH1004 or from a progeny or ancestor of said line comprising said trait. Accordingly, based on the description of the present invention, the skilled person in possession of pepper hybrids Y1194, deposited under accession no. NCIMB 41187, or line ZORO.27.42.7:DH1004 has no difficulty transferring the trait of extended storability of the present invention to other pepper plants of various types using breeding techniques well-known in the art, and thereby extending the storability of the fruits of said pepper plant. The trait of the present invention is for example transferred to pepper plants producing fruit of various types or shapes, such as bell peppers or sweet peppers, big rectangular peppers, conical peppers, including long conical peppers, or blocky-type peppers and of various mature colors, such as red, yellow, orange or ivory. Accordingly, in one embodiment, a plant of the present invention is a *C. annuum* plant is capable of producing a fruit, which is a bell pepper or sweet pepper, a big rectangular pepper, a conical pepper or a long conical pepper according to the instant invention. In one embodiment, a plant of the present invention is capable of producing a red, yellow, orange or ivory pepper fruit according to the instant invention. In another embodiment, different sources for a trait of the present invention are combined, for example by crossing two plants of the present invention. In one embodiment, a trait of the present invention derived from hybrid Y1194, or an ancestor or progeny thereof is combined with a trait of the present invention derived from line ZORO.27.42.7:DH1004, or an ancestor or progeny thereof. In one embodiment, the shelf-life on the plant of fruits of a plant resulting from such a combination is further increased when compared to its parents.

Accordingly, in another embodiment, the present invention discloses a method of transferring a trait of extended storability according to the present invention to a pepper plant lacking said trait comprising a) obtaining a plant comprising said trait; b) crossing it to a plant lacking said trait; c) obtaining plants of the cross of step b); d) selecting a plant of step c) which is capable of producing fruits with extended storability according to the present invention. In one embodiment, the method further comprises e) back-crossing a plant resulting from step d) with a pepper plant, and f) selecting for a pepper plant, which is capable of producing fruits with extended storability according to the present invention. In one embodiment, the method further comprises obtaining an inbred pepper plant, which is capable of producing fruits with extended storability according to the present invention, and, in one embodiment, the further comprises crossing said inbred pepper plant to another pepper plant to produce a hybrid pepper plant, which is capable of producing fruits with extended storability according to the present invention. In one embodiment, a pepper plant is selected by determining the marketability, firmness, resistance to wilting, resistance to climacteric degradation or brightness of its fruits over time, as described herein. In one embodiment, the, the plant of step a) comprising said trait is a plant of hybrid Y1194 or a progeny or ancestor of said plant, or a plant of line ZORO.27.42.7:DH1004 or a progeny or ancestor of said plant. In one embodiment, the plant of step a) comprising said trait is a progeny of hybrid Y1194 and line ZORO.27.42.7:DH1004, or a progeny thereof.

In one embodiment, the present invention discloses a *C. annuum* plant obtainable by any one of the methods above, wherein the plant is capable of producing a fruit as described herein. In yet another embodiment, the present invention discloses a method of producing a plant comprising a trait of extended storability according to the present invention to a pepper plant lacking said trait comprising a) obtaining a plant comprising said trait; b) crossing it to a plant lacking said trait; c) obtaining plants of the cross of step b); d) selecting a plant of step c) which is capable of producing fruits with extended storability according to the present invention. In one embodiment, the method further comprises e) back-crossing a plant resulting from step d) with a pepper plant, and f) selecting for a pepper plant, which is capable of producing fruits with extended storability according to the present invention. In one embodiment, the method further comprises obtaining an inbred pepper plant, which is capable of producing fruits with extended storability according to the present invention, and, in one embodiment, further comprises crossing said inbred pepper plant to another pepper plant to produce a hybrid pepper plant, which is capable of producing fruits with extended storability according to the present invention. In one embodiment, a pepper plant is selected by determining the marketability, firmness, resistance to wilting, resistance to climacteric degradation or brightness of its fruits over time, as described herein. In one embodiment, the, the plant of step a) comprising said trait is a plant of hybrid Y1194 or a progeny or ancestor of said plant, or a plant of line ZORO.27.42.7:DH1004 or a progeny or ancestor of said plant. In one embodiment, the plant of step a) comprising said trait is a progeny of hybrid Y1194 and line ZORO.27.42.7:DH1004, or a progeny thereof.

In one embodiment, the present invention discloses a *C. annuum* plant obtainable by any one of the methods above, wherein the plant is capable of producing a fruit as described herein. Based on the teachings of the present invention, a skilled person can design a program to look for new sources for a trait according to the present invention. For example, in such program, plant are grown in nurseries and are scored at the end of the crop to identify lines or individual plants with a commercially acceptable appearance of the fruit (e.g. firmness, smoothness, brightness). The progenies of these selected lines or individual plants are scored in the next nursery for the same characteristics but with the addition of the maturity date (mean of the line, weekly notation). When the data are still positive, the next nursery is more detailed and the storability on the plant is scored as described herein. In one embodiment, selected candidates are used in a breeding program to produce a plant according to the present invention.

In another embodiment, the present invention also discloses a method of extending the storability of a fruit of a pepper plant comprising introducing into said pepper plant a trait according to the instant invention. In one embodiment, said trait is derived or obtainable from pepper line Y1194, from line ZORO.27.42.7:DH1004, or from a progeny of hybrid Y194 and line ZORO.27.42.7:DH1004. In one embodiment, the fruit is as described herein. In one embodiment, present invention discloses a *C. annuum* plant capable of producing a fruit as described herein, wherein the plant is obtainable by the process of crossing a *C. annuum* plant with a plant of hybrid Y1194 or a progeny or ancestor thereof, or a plant of line ZORO.27.42.7:DH1004 or a progeny or ancestor thereof and selecting for a *C. annuum* plant capable of producing a fruit as described herein.

In one embodiment, the genetic information determining the trait of extended storability according to the instant invention comprises a dominant gene. This gene is on a locus that is obtainable from pepper line Y1194, deposited under deposited under accession no. NCIMB 41187, or from a progeny or ancestor of said line comprising said trait. In one embodiment, this locus is obtained or derived from pepper line Y1194, deposited under deposited under accession no. NCIMB 41187, or from a progeny or ancestor of said line comprising said trait. In one embodiment, the genetic information determining the trait of extended storability according to the instant invention obtainable from hybrid Y1194 or from line ZORO.27.42.7:DH1004. Using the teaching of the present invention, such genetic information is transferred to another plant, for example by crossing said plant with hybrid Y1194, line ZORO.27.42.7:DH11004, or an ancestor or progeny thereof, and determining the presence of the trait of the present invention in the progeny of the cross.

Traits, in particular traits with a phenotype that can be scored, such as a resistance to a particular condition, can be followed genetically through crosses and the segregation of the trait can be scored in the progeny resulting from the cross. This allows, for example, one to determine whether a trait is dominant, recessive, or partially dominant. This also allows one to test whether genes determining a trait are at the same locus or at different linked or unlinked loci. This also allows one to test whether a trait is monogenic or polygenic.

For example, when a plant homozygous for a trait is crossed with a "tester" plant homozygous for a dominant trait having the same phenotype, the progeny of the cross does not segregate for the phenotype of the trait (1:0 ratio). This 1:0 ratio is scored when the genes for the trait are at the same locus or at different loci. When the first generation progeny plants of the cross above are self-pollinated, a 1:0 ratio is observed for dominant traits based on genes at the same locus for the plant to be tested and for the "tester" plant. In contrast, a 15:1 ratio is observed for dominant traits based on genes at different, unlinked loci for the plant to be tested and for the "tester" plant. If the genes are at different loci but genetically linked the ratio is generally between these 1:0 and 15:1.

In another example, when a plant to be tested, which is heterozygous for a dominant trait, is crossed with a "tester" plant, which is also heterozygous for the dominant trait having the same phenotype, the progeny of the cross segregates 3:1 for the resistant phenotype. This 3:1 ratio is scored when the genes for the trait are at the same locus or at different loci. When the first generation progeny plants of the cross above are self-pollinated, second generation progenies of individual plants for genes at the same locus, give 50% of the offspring plants again segregating 3:1, 25% 1:0 and 25% 0:1. With an unlinked genes in the plant to be tested, in the second generation, after self-pollination, individual plants give 50% of the offspring plants again segregating 3:1, 25% 15:1, and 25% 0:1 (no plant fixed for the trait in the second generation).

Other crossing strategies are also used, e.g. with other combinations of homozygous or heterozygous plants, or with plants not comprising the trait. Segregation of the trait in the progeny is then scored. These crossing strategies and their corresponding segregation ratios are well known to the person skilled in the art, who also knows how to obtain and use appropriate "tester" plants, and how to interpret segregation ratios obtained from such crosses. In another embodiment, the crossing schemes illustrated above are applied to the trait of the instant invention.

Commercial peppers are generally hybrids produced from the cross of two parental lines (inbreds). The development of hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc.

A single cross hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

Breeding in peppers can be accelerated by the use of double haploids obtained by anther culture. Such a technique gives the possibility to secure the process by producing pure lines in a shorter period of time than the regular pedigree breeding process.

Plants within the *Capsicum annuum* species can be easily cross-pollinated. A trait is also readily transferred from one pepper plant to another plant, including pepper plants of different types using conventional breeding techniques, for example to further obtain commercial lines. The introgression of a trait into the elite line is for example achieved by recurrent selection breeding, for example by backcrossing. In this case, the elite line (recurrent parent) is first crossed to a donor inbred (the non-recurrent parent) that carries the trait. The progeny of this cross is then mated back to the recurrent parent followed by selection in the resultant progeny for the trait. After three, preferably four, more preferably five or more generations of backcrosses with the recurrent parent with selection for the trait, the progeny is heterozygous for the locus harboring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for the trait is carried out after each cross. Male sterility is available in pepper. In particular genetic male sterility is widely using in commercial lines (see for example Daskaloff S. (1972) Male sterile pepper mutants and their utilization in heterosis breeding. Eucarpia, meetings on genetic and breeding. Turin 1971, 205-210).

Accordingly, in one embodiment, a plant of the present invention is an inbred, a hybrid, or a dihaploid, in one embodiment produced by pedigree breeding or by recurrent selection breeding. In one embodiment, a plant of the present invention has commercially acceptable agronomic characteristics.

In another embodiment, the present invention discloses a method of producing seed of a pepper plant of the present invention comprising: a) growing a plant of the present invention; b) allowing said plant to self-pollinate; c) harvesting seeds from said plant.

Pepper plants can also be propagated vegetatively, for example through grafting using methods well-known in the art. Accordingly, the instant invention discloses a method of propagating a pepper plant according to the present invention comprising: a) collecting a part of a plant of the present invention; b) grafting a part of said plant onto another pepper plant. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets; d) growing plants from said rooted plantlets; and harvesting seeds from said plants.

Pepper plants of the present invention can also be transformed genetically with a gene of interest, as for example described in U.S. Pat. No. 5,945,580.

The inventors of the instant invention are first to recognize that a fruit of a pepper plant can be stored on a plant and thus that the harvest of the fruit can be delayed. This brings a number of benefits to growers and to the parties involved in the pepper business chain.

In one embodiment, a plant of the present invention allow for a longer harvest period while maintaining high fruit quality and avoiding losses. Plants of the present invention also allow for a lower harvest frequency of the crop. Thus, the present invention offers the possibility for a grower to harvest less often a higher fruit quantity per plant or per surface area. This allows for a better planning of the harvest, a better planning of labor, a better efficiency of the harvest and more ripe fruits per harvest, while keeping the same fruit quality. A better efficiency and flexibility in the production of pepper fruit is possible. The present invention also allows for better planning for grading and packing of the product, and for better planning for sales and delivery of the product, thereby substantially reducing losses in the business chains and production costs.

In one embodiment, the present invention allows to delay harvest of the fruit, depending on the needs of the market, on the price offered for pepper fruits, on the availability of post-harvest storage, on the availability of labor or on appropriate transport to the consumer or a combination thereof. In one embodiment, the use of post-harvest storage is avoided or substantially reduced. This reduces costs and also allows to use the post-harvest shelf-life of the peppers further down the business chains, e.g. in a retail store or to benefit customers.

For example, the production of blocky pepper in the Netherlands is in waves. This leads to low prices during periods of high production and high prices during periods of low production. The differences between low and high prices can be 100% or more. Plants of the instant invention benefit the grower, because of a better planning to deliver on demand, a better planning and lower costs for labor with a more stable harvest and the possibility to wait for better prices during periods of high production. This also allows growers to deliver a constant harvest at fixed prices.

For example, in Dutch glasshouses, the standard harvest is once per week, where the production is typically between about 0.3 and about 2.0 kg per harvest per $m^2$. For example, a grower could harvest about 1 kg per week per $m^2$ over a certain period of time by planting a plant of the present invention.

Plants of the instant invention also benefit the distributors because they can assure constant supply of fresh produce and have better planning, and thus saving on costs. In one embodiment, distributors can also offer these products at a higher price.

Accordingly, the present invention further discloses a method of storing *Capsicum annuum* fruits comprising: a) growing a *Capsicum annuum* plant; b) allowing said plant to set fruit; c) storing said fruit on said plant. In one embodiment, the method further comprises: d) harvesting said fruit. In one embodiment, the fruit is stored on the plant for about 3 weeks after full coloring of the fruit. In one embodiment, the fruit is stored on the plant for about 4 weeks, in one embodiment for about 5 weeks, in one embodiment for about 6 weeks after full coloring of the fruit. In one embodiment, about 100% of said fruit is marketable. In one embodiment, the *Capsicum annuum* plant of step a) is a plant according to the present invention. In one embodiment, the fruit is stored on the plant for a time period set forth herein. In one embodiment, the fruit is stored on the plant under the conditions set forth herein. The present invention also further discloses a method of extending the harvest time of a pepper fruit comprising: a) growing a *Capsicum annuum* plant; b) allowing said plant to set fruit; c) delaying the harvest of the fruit; d) harvesting the fruit. In one embodiment, the harvest of said fruit is delayed for about 3 weeks after full coloring of the fruit, in one embodiment for about 4 weeks, in one embodiment for about 5 weeks, after full coloring of the fruit. In one embodiment, the harvest of the fruit is delayed up to about six weeks after full coloring of the fruit. In one embodiment, about 100% of the fruit is marketable. In one embodiment, the *Capsicum annuum* plant of step a) is a plant according to the present invention. In one embodiment, the harvesting of the fruit is delayed for a time period set forth herein. In one embodiment, the fruit is stored on the plant under the conditions set forth herein.

The present invention also further discloses a method of making a harvest decision comprising: a) determining when a fruit of a *C. annuum* plant has reached full coloring; b) comparing the supply for a pepper crop on a market to a target supply for a pepper crop; c) deciding to delay the harvest of the fruit until the supply for a pepper crop on a market has reached, or is below, the target supply. In one embodiment, the method further comprises harvesting the fruit when the supply for a pepper crop has reached or is below the target supply. In one embodiment, the harvest of said fruit is delayed for up to six weeks after full coloring of said fruit. In one embodiment, the harvest of said fruit is delayed for up to 5 weeks after full coloring of said fruit. In one embodiment, the harvest of said fruit is delayed for up to 4 weeks after full coloring of said fruit. In one embodiment, the harvest of said fruit is delayed for at least 3 weeks after full coloring of said fruit. In one embodiment, the harvest of said fruit is delayed for at least 4 weeks after full coloring of said fruit. In one embodiment, the harvest of said fruit is delayed for at least three weeks after full coloring of said fruits, wherein about 100% said fruits remain marketable. In one embodiment, the harvest of said fruit is delayed for up to 4 weeks after full coloring of said fruit. In one embodiment, the harvest of said fruit is delayed for at least 3 weeks after full coloring of said fruit. In one embodiment, the harvest of said fruit is delayed for at least 4 weeks after full coloring of said fruit. In one embodiment, the harvest of said fruit is delayed for at least 4 weeks after full coloring of said fruit, wherein about 90% said fruits remain marketable. In one embodiment, the harvest of said fruit is delayed for at least 5 weeks after full coloring of said fruit, wherein about 90% said fruits remain marketable. In one embodiment, the *C. annuum* plant is a plant according to the present invention. In one embodiment, the harvesting of the fruit is delayed for a time period set forth herein. In one embodiment, the fruit is stored on the plant under the conditions set forth herein. In one embodiment, said step c) comprises making a harvest decision.

The present invention also further discloses a method of making a harvest decision comprising: a) determining when a fruit of a *C. annuum* plant has reached full coloring; b) comparing the price for a pepper fruit on a market to a target price for a pepper fruit; c) deciding to delay the harvest of the fruit in the hope that the price for a pepper fruit on a market has reached, or exceeds, the target price. In one embodiment, the method further comprises harvesting the fruit when the price for a pepper fruit has reached or exceeds the target price. In one embodiment, the harvest of said fruit is delayed for up to six weeks after full coloring of said fruit. In one embodiment, the harvest of said fruit is delayed for up to 5 weeks after full coloring of said fruit. In one embodiment, the harvest of said fruit is delayed for up to 4 weeks after full coloring of said fruit. In one embodiment, the harvest of said fruit is delayed for at least 3 weeks after full coloring of said fruit. In one embodiment, the harvest of said fruit is delayed for at least 4 weeks after full coloring of said fruit. In one embodiment, the harvest of said fruit is delayed for at least three weeks after full coloring of said fruits, wherein about 100% said fruits remain marketable. In one embodiment, the harvest of said fruit is delayed for up to 4 weeks after full coloring of said fruit. In one embodiment, the harvest of said fruit is delayed for at least 3 weeks after full coloring of said fruit. In one embodiment, the harvest of said fruit is delayed for at least 4 weeks after full coloring of said fruit. In one embodiment, the harvest of said fruit is delayed for at least 4 weeks after full coloring of said fruit, wherein about 90% said fruits remain marketable. In one embodiment, the harvest of said fruit is delayed for at least 5 weeks after full coloring of said fruit, wherein about 90% said fruits remain marketable. In one embodiment, the *C. annuum* plant is a plant according to the present invention. In one embodiment, the harvesting of the fruit is delayed for a time period set forth herein. In one embodiment, the fruit is stored on the plant under the conditions set forth herein. In one embodiment, said step c) comprises making a harvest decision.

In another embodiment, the harvest decision is made after evaluating the availability of labor to harvest said fruit or evaluating the availability of transport means to transfer said pepper fruit to a third party or both, or in conjunction with the supply or the price of the crop in a market or both.

In another embodiment, the present invention discloses a method of increasing the return of a pepper crop comprising: a) determining when a fruit of a *C. annuum* plant has reached full coloring; b) comparing the price for a pepper crop on a market to a target price for a pepper crop; c) delaying the harvest of said fruit until the price for a pepper crop on a market has reached, or exceeds, said target price; d) selling said pepper crop at or above said target price. In one embodiment, the *C. annuum* plant is a plant according to the present invention. In another embodiment, the present invention discloses a method to assure the supply of a pepper produce comprising: a) contracting a party to grow a pepper plant; b) comparing the supply of pepper fruit in a market to a set level; c) instructing said party to harvest fruit from said plant when the supply of pepper fruit in said market falls below said set level. In one embodiment, the pepper fruit is stored on the plant for at least three weeks after full coloring, wherein about 100% of said fruit is still marketable. In one embodiment, the pepper plant is a plant according to the present invention. In one embodiment, the party is a grower.

In another embodiment, the present invention discloses a method to assure the supply of a fresh produce in a market comprising: a) contracting a party to provide a constant supply of pepper fruit over a period of time; b) paying said party a premium for providing a constant supply of said pepper fruit over said period of time. In one embodiment, the party is a grower. In one embodiment, the pepper fruit is a fruit of a plant according to the present invention.

All references cited herein are incorporated by reference in the application in their entireties.

The following examples are intended to provide illustrations of the application of the present invention. The following examples are not intended to completely define or otherwise limit the scope of the invention.

EXAMPLES

Example 1

Breeding History of Pepper Hybrid Y1194

Pepper hybrid Y1194 is a male sterile F1 hybrid developed by Syngenta Seeds in Holland. It is a fresh market pepper of the Sweet Bell type.

The female parent of Y1194 is male sterile line 4P181, a proprietary Syngenta Seeds line. Line 4P181 was obtained through 7 generations of self-pollination of commercial hybrid FIESTA (Enza Zaden, Enkhuizen, The Netherlands).

The male parent of Y1194 is line 4P287, also a proprietary Syngenta Seeds line. Line 4P287 was obtained by the following series of crosses. Line 9948, a proprietary Syngenta Seeds line which may be derived from a blocky yellow pepper hybrid from de Ruiter (Bergschenhoek, The Netherlands) comprising the L3 gene conferring resistance to pepper mild mottle virus, was crossed with BLONDY, a commercial hybrid of Syngenta Seeds. The progeny of this cross was self-pollinated for three generations. One of the resulting progenies was crossed with a progeny resulting from three generations of self-pollination of FIESTA. A progeny resulting from the later cross was self-pollinated over 6 generations to obtain line 4P287.

Example 2

Description of Pepper Line Y1194

A description of hybrid Y1194 is shown in Table 1. The characteristics below were recorded for plants grown in glasshouse.

TABLE 1

Characteristics of hybrid Y1194

| | | |
|---|---|---|
| Plant: hypocotyl coloration | 1 absent/9 present. | 9 |
| Plant: length of stem (from cotelyledons to first flower/branching) | 3 short/5 medium/7 long. | 5 |
| Plant: hairiness | 1 absent or very weak/3 weak/ 5 medium/7 strong/ 9 very strong. | 1 |
| Plant: shortened internode | 1 absent (indeterminant)/ 9 present (determinant). | 1 |
| Plant: vigour | 1 very weak/3 weak/5 medium/ 7 strong/9 very strong. | 5 |
| Plant: height | 1 very compact/3 compact/ 5 medium/7 high/ | 5 |
| Flower: attitude of peduncle | 1 erect/2 non-erect. | 2 |
| Fruit: color before maturity | 1 greenish white/2 yellowish/ 3 green/4 purple. | 3 |
| Fruit: intensity of color before maturity | 1 very light/3 light/5 medium/ 7 dark/9 very dark. | 1 |
| Fruit: ratio longitud/width | 1 very short/3 compact/5 medium/ 7 high/9 very high. | 5 |
| Fruit: length | 1 very short/3 short/5 medium/ 7 long/9 very long. (8 cm) | 5 |
| Fruit: diameter | 1 very small/3 small/5 medium/ 7 large/9 very large. (8 cm) | 5 |
| Fruit: size | 1 very small/3 small/5 medium/ 7 big/9 very big. | 5 |
| Fruit: predominant shape of longitudinalsection | 1 flattened/2 round/3 heartshaped/ 4 square/5 rectangular/6 trapezoid/ 7 triangular/8 narrow triangular/ 9 hornshaped | 4 |
| Fruit: predominant shape in transversal section (at level of placenta) | 1 elliptic/2 triangular/ 3 quandrangular/4 circular. | 3 |
| Fruit: shape | 1 flat/2 heart shaped/3 rectangular/ 5 rectangular-trapezoid/ 6 trapezoid/8 triangular/ 9 horn shaped. | 3 |
| Fruit: color at maturity | 1 yellow/2 orange/3 red/4 brown | 1 |
| Fruit: intensity of color at maturity | 1 very light/3 light/5 medium/ 7 dark/9 very dark. | 3 |
| Fruit: shape of stalk side | 1 globe/3 flat/5 little depressed/ 7 depressed/9 very depressed. | 5 |
| Fruit: shape of apex | 1 very depressed/2 depressed/ 3 somewhat depressed/4 smooth/ 5 round/8 sharp/9 very sharp. | 4 |
| Fruit: thickness of pericarp | 1 very thin/3 thin/5 medium/ 7 thick/9 very thick. | 7 |
| Fruit: predominant number of locules | 1 only two/2 two and three/ 3 three and four/4 four and more. | 3 |
| Fruit: length of stalk | 3 short/5 medium/7 long. | 5 |
| Fruit: capsaicin in placenta | 1 absent/9 present. | 1 |

TABLE 1-continued

Characteristics of hybrid Y1194

| | | |
|---|---|---|
| Time of beginning of first flowering (1st flower on 2nd flowering node on 50% of plants) | 3 early/5 medium/7 late. | 3 |
| Time of ripening (color change of fruits on 50% of plants) | 1 very early/3 early/5 medium/ 7 late/9 very late. | 5 |

Example 3

Growth Conditions of Pepper Plants

Plants were grown in Dutch heated glasshouse. Sowing was done following standard methods using rockwool plugs (Tray T 240, plug PL 2027, Cultilène, Bleiswijk, The Netherlands). After 2 weeks, seedlings were transplanted in 10 cm rockwool blocks (reference B0353, Cultilène, Bleiswijk, The Netherlands). 5 weeks after sowing the transplants were planted on rockwool slabs 200×20×10 cm (Cultilène, Bleiswijk, The Netherlands) according to a standard Dutch growing system with 8 rows per 6.40 m wide glasshouse construction, 3 plants per square meter, and 2 stems per plant.

The average growth conditions in the glasshouse were as follows:

Average day temperature: 23.3° C., average night temperature: 18.5° C., average temperature per 24 hour period: 21.1° C.

Average day relative humidity: 74.4%, average night relative humidity: 78.7%, average relative humidity per 24 hour period: 75.6%.

Average day $CO_2$ concentration: 500 ppm, average night $CO_2$ concentration: 578 ppm, average $CO_2$ concentration per 24 hour period: 536 ppm.

Example 4

Extended Storability on the Plant of Pepper Fruits of Hybrid Y1194

Plants were grown as described above in example 3. Hybrid Y1194, which produces yellow fruits, was compared to standard hybrid Sprinter, which produces red fruits. The observations on fruits set were made on 8 plants per line, in total for about 30 fruits per line. The first fruit setting was observed 9 weeks after sowing for Y1194, and 10 weeks after sowing for Sprinter. The first fruit with full coloring on the plant was observed 16 weeks after sowing for Y1194, and 17 weeks after sowing for Sprinter. Setted fruits of 1-2 cm in size were labelled at the beginning of each week and the week number noted. In total at least 5 fruits per plant were followed through the experiment.

At start of the fruit coloring of these fruits, the week number was noted in the beginning of each week number of full color stage of the fruits. Only fruits considered marketable at the time of full coloring where followed and scored.

4.1. Marketability of Fruits Kept on the Plant

Table 2 shows the percentage of marketable fruits in weeks after full coloring on the plant for Y1194 and Sprinter. Marketable fruits were judged for their appearance and on how they would appeal to consumers.

After full coloring each fruit was checked weekly visually. About 30 fruits per line were followed.

TABLE 2

| | Weeks after full coloring on the plant | | | | | |
|---|---|---|---|---|---|---|
| | 2 | 3 | 4 | 5 | 6 | 8 |
| Sprinter | 100 | 75 | 10 | 0 | 0 | 0 |
| Y1194 | 100 | 100 | 100 | 100 | 100 | 60 |

Table 2 shows that about 100% of fruits of Y1194 are still marketable 6 weeks after full coloring on the plant. This shows extended storability for fruits of Y194 compared to fruits of Sprinter.

4.2. Firmness of Fruits Kept on the Plant

Table 3 shows the firmness of fruits of Y1194 and Sprinter in weeks after full coloring on the plant. After full coloring each fruit was controlled by hand on firmness and recorded on a 0-9 scale as described below. About 20 fruits per hybrid were followed.

TABLE 3

| | Weeks after full coloring on the plant | | | | | |
|---|---|---|---|---|---|---|
| | 2 | 3 | 4 | 5 | 6 | 8 |
| Sprinter | 5 | 4 | 1 | 0 | 0 | 0 |
| Y1194 | 5 | 5 | 5 | 5 | 5 | 3 |

Table 3 shows that the firmness of fruits of Y1194 is retained for an extended period of time when compared to Sprinter, with about 100% of fruits of Y1194 retaining their firmness 6 weeks after full coloring.

The firmness of pepper fruits was scored manually on a scale ranging from 0 to 9, with:
0: very soft
1: quite soft, very limited resistance to finger pressure
2: "spongy" consistency, for example as in F1 hybrid Orobelle (Syngenta Seeds)
3: intermediate between elastic and spongy
4: elastic but resistant to high finger pressure, for example as in F1 hybrid Volga (Syngenta Seeds)
5: reasonable medium firmness
6: superior firmness, as for example in F1 hybrid Roxy (Syngenta Seeds) when grown in winter conditions in Spain
7: superior firmness, limited deformation of the wall to a high finger pressure
8: extremely firm, also described as "stony pepper", almost no deformation of the wall to a high finger pressure
9: extremely firm, also described as "stony pepper", flesh fully resists to a high finger pressure Alternatively, a 1-5 scale is used to determine the firmness of a fruit as described in (Miller et al. (1983) Proc. Fla. State Hort. Soc. 96: 345-350) or in (Gonzalez-Aguilar et al (1999) Journal of Food Quality 22: 287-299). This 1-5 scale defines the firmness of a fruit as: 1=flaccid, 2=slightly firm, 3=moderately firm, 4=firm, 5=very firm.

Alternatively, the firmness of a fruit is measured using a firmness tester, as for example described in Gonzalez and Tiznado (1993) Lebensm.-Wiss. u.-Technol. 26: 450-455. The firmness tester described therein is a Chatillon Model DFG 50, John Chatillon & Sons, Inc., New York, N.Y. Additional firmness testers are also described in Hampshire-TJ et al. American-Society-of-Agricultural-Engineers. 1987, No. 87-6005, 19 pp.

4.3. Wilting of the Fruits Kept on the Plant

Table 4 shows fruit wilting for fruits of Y1194 and Sprinter in weeks after full coloring on the plant. After full coloring each fruit was recorded on a 1-5 scale as described above. About 20 fruits per hybrid were followed.

TABLE 4

| | Weeks after full coloring on the plant | | | | | |
|---|---|---|---|---|---|---|
| | 2 | 3 | 4 | 5 | 6 | 8 |
| Sprinter | 0 | 25 | 90 | 100 | 100 | 100 |
| Y1194 | 0 | 0 | 0 | 0 | 0 | 40 |

The table shows the percentage of fruits scored 4 or less than 4 in the scale above. Essentially no fruit of Y1194 exhibited wilting 6 weeks after full coloring. Wilting of the fruits was determined according to the scale below:

| Scale: | |
|---|---|
| 5 | Smooth |
| 4 | 20% of the surface affected by wilting |
| 3 | 40% of the surface affected by wilting |
| 2 | 60% of the surface affected by wilting |
| 1 | 80% of the surface affected by wilting |
| 0 | 100% of the surface affected by wilting |

4.4. Resistance to Climacteric Degradation of Fruits Kept on the Plant

Table 5 describes the resistance to climacteric degradation of fruits of Y1194 and Sprinter recorded in weeks after full coloring on the plant.

TABLE 5

| | Weeks after full coloring on the plant | | | | | |
|---|---|---|---|---|---|---|
| | 2 | 3 | 4 | 5 | 6 | 8 |
| Sprinter | 0 | 10 | 20 | 35 | 35 | 35 |
| Y1194 | 0 | 0 | 0 | 0 | 0 | 0 |

Table 5 shows the percentage of fruits showing more than 5 yellow spots. 20 fruits per hybrid were observed. Table 5 shows that even 8 weeks after full coloring on the plant essentially all fruits of Y1194 show less than 5 yellow spots per fruit.

4.5. Brightness of Fruits Kept on the Plant

Table 6 describes the brightness of fruits of Y1194 and Sprinter in weeks after full coloring on

TABLE 6

| | Weeks after full coloring on the plant | | | | | |
|---|---|---|---|---|---|---|
| | 2 | 3 | 4 | 5 | 6 | 8 |
| Sprinter | 0 | 25 | 90 | 100 | 100 | 100 |
| Y1194 | 0 | 0 | 0 | 0 | 0 | 40 |

Table 6 indicates the percentage of fruits scored 2 or less than 2 on a 0-5 scale described above. 20 fruits per hybrid were observed. Table 6 shows that essentially all fruits of Y1194 exhibit acceptable brightness 6 weeks after full coloring. Brightness of the fruits was determined visually according to the scale below:

| Scale: | |
|---|---|
| 5 | shinning, looking fresh |
| 4 | about 90% of the fruit surface still shining |
| 3 | about 70% of the fruit surface still shining |
| 2 | about 50% of the fruit surface still shining |
| 1 | about 20% of the fruit surface still shining |
| 0 | dull, not shinning, looking "old" |

A level of 3 or more in the above scale is considered acceptable.

Example 5

Thickness of the Wall of Pepper Fruits

Mature fruits of pepper plants were cut open. The wall thickness of the fruits was measured on the thinnest part of the wall of the fruits. The fruits of 6 hybrids were measured with 10 mature fruits measured per hybrid. The size of the fruits varied between 70-85 mm in width.

The measurements were made in hot summer conditions. In spring conditions walls are expected to be generally thicker.

| Hybrid: | Thickness in mm: | Remarks: |
|---|---|---|
| Sprinter | 5.3 | Average fruit size slightly smaller than Y 1194 |
| Y1194 | 6.92 | |
| Y1301 | 7.33 | In average bigger fruits than Y 1194 |
| Ottavo | 5.10 | Syngenta Seeds yellow hybrid known as thin walled |
| Bossanova | 5.80 | Hybrid of Rijk Zwaan (Enkhuizen, The Netherlands) with known low post harvest storability |
| Troppo | 4.92 | Syngenta Seeds red hybrid known as thin walled with low post-harvest storability |

Example 6

Post-Harvest Marketability of Fruits of Y1194

Pepper plants of hybrid Y1194 were grown as described in example 3. Mature pepper fruits were stored directly after harvest at about 16 to about 18° C., and evaluated at 10-12, 16-18 and 22-24 days after harvest. Fruits of hybrid Y1194 retained marketability.

Example 7

Post-Harvest Storability of Fruits of Y1194

Pepper plants of hybrid Y1194 are grown as described in example 3. Mature pepper fruits are stored directly after harvest at about 16 to about 18° C. The fruits are evaluated daily starting after harvest until day 40 after harvest. The characteristic of the pepper fruits are measured as described herein, in particular marketability, firmness, resistance to wilting, resistance to climacteric degradation, brightness.

Example 8

Post-Harvest Storability of Fruits of Y1301

Pepper plants hybrid Y1301 are grown as described in example 3. Mature pepper fruits are stored directly after harvest at about 16 to about 18° C. The fruits are evaluated daily starting after harvest until day 40 after harvest. The characteristic of the pepper fruits are measured as described herein, in particular marketability, firmness, resistance to wilting, resistance to climacteric degradation, brightness.

Example 9

Post-Harvest Storability in a Typical Pepper Business Chain

Pepper plants are grown in the open field or in a greenhouse as described in Example 3 above.

Pepper fruits are subjected to the following conditions, representing the typical pepper business chain until fruits reach the consumers.

HARVEST, FIELD, 25-30° C., 0,5-0,5d

PACKING, PACKING STATION, 18° C., 0,5-1d

PRECOOLING, CHAMBER, 8° C., 0,25-0,5d

TRANSPORT, COOLED TRUCKS, 10° C., 2-3d

RECEPTION, PLATFORM SUPERMARKET, 12° C., 0,5-1d

SALES, SUPERMARKET, 17-18° C., 1-2d

CONSUMTION, HOME/FREEZER, 5-18° C., 14d

The marketability of the fruits is determined as described herein after each step and at the end of the trial. Other characteristic of the fruits, such as firmness of the fruit, the presence or absence of climacteric spots, brightness, or wilting of the fruit are also determined as described herein after each step and at the end of the trial.

Fruits of pepper line Y1194 are assessed.

Fruits of pepper line Y1301 are assessed.

Example 10

Extended Storability on the Plant of Pepper Fruits of Hybrid Y1301

Pepper plants of hybrid 1301 are grown as described in example 3 above. The storability of fruits of Y1301 is determined as described in example 4 above.

Example 11

Growth Conditions of Pepper Plants

Plants were grown in Dutch heated glasshouse according to example 3, with the following average growing conditions:

Average day temperature: 25.2 C, average night temperature: 20.3 C average temp per 24 hour period 23.5 C Average day relative humidity: 69%, average night relative humidity: 80%, average relative humidity per 24 hour period; 73%

Average day $CO_2$ concentration 596 ppm, average night $CO_2$ concentration 502 ppm, average $CO_2$ concentration 563 ppm.

Example 12

Extended Storability on the Plant of Pepper Fruits of Hybrid Y1194

Plants were grown as described above in example 11. Fruits of standard variety Sprinter, hybrid Y1194, and F3 progeny plants of hybrid Y1194 were evaluated. F3 progeny plant originating from the same F2 plant were grouped together (5865-5869). The first fruit setting was observed 9 weeks after sowing for Y1194, and 10 weeks after sowing for Sprinter (how about the F3 plants?). The first fruit with full coloring on the plant was observed 16 weeks after sowing for Y1194, and 17 weeks after sowing for Sprinter. Setted fruits of 1-2 cm in size were labelled at the beginning of each week and the week number noted.

At start of the fruit coloring of these fruits, the week number was noted in the beginning of each week number of full color stage of the fruits. Only fruits considered marketable at the time of full coloring where followed and scored. It is noted that about 8 fruits of Y1194 showed some symptoms of fruitrot, but were included in the study and in the table below. The symptoms of fruitrot generally lowered the scores given to these fruits.

Marketability of Fruits Kept on the Plant

Table 7 shows the percentage of marketable fruits in weeks after full coloring on the plant for Sprinter, Y1194 and 5 groups of F3 progeny plants of Y1194. Marketable fruits were judged for their appearance and on how they would appeal to consumers. In particular, when lack of firmness, wilting, climacteric degradation, or lack of brightness as described herein was observed, the fruits were judged as not marketable.

After full coloring each fruit was checked weekly. The following number of plants and fruits were evaluated and are reported in Table 7:

Sprinter: 4 plants, 22 fruits; Y1194: 8 plants, 44 fruits; 5865: 6 plants, 31 fruits; 5866: 6 plants, 29 fruits; 5867: 5 plants, 22 fruits; 5868: 6 plants, 39 fruits; 5869: 4 plants, 20 fruits.

TABLE 7

| | Weeks after full coloring on the plant | | | | | | |
|---|---|---|---|---|---|---|---|
| | 2 | 3 | 4 | 5 | 6 | 7 | 8 |
| Sprinter | 100 | 90 | 50 | 0 | 0 | 0 | 0 |
| Y1194 | 100 | 100 | 98 | 88 | 63 | 38 | 10 |
| 5865 | 100 | 94 | 55 | 16 | 13 | 6 | 0 |
| 5866 | 100 | 100 | 93 | 72 | 55 | 21 | 14 |
| 5867 | 100 | 100 | 100 | 91 | 77 | 68 | 45 |
| 5868 | 100 | 100 | 97 | 92 | 59 | 49 | 23 |
| 5869 | 100 | 100 | 100 | 100 | 90 | 75 | 30 |

Table 7 shows for example that about 100% of fruits of Y1194 are still marketable 4 weeks after full coloring on the plant, and that about 90% of the fruits of Y1194 are still marketable 5 weeks after full coloring on the plant. This shows extended storability for fruits of Y1194 compared to fruits of Sprinter. Table 7 also shows that the trait of extended storability on the plant is transmitted to the next progeny of hybrids Y1194. For example, about 100% of fruits of the plants in group 5869 are still marketable 5 weeks after full coloring on the plant, and about 90% of fruits of the plants in group 5869 are still marketable 6 weeks after full coloring on the plant.

TABLE 8

The data in Table 8 shows the raw data for the fruits used in Table 7. A number in Table 8 indicated the number of weeks after which the fruit evaluated was no longer marketable. For example, a "5" means that a fruit was no longer marketable after 5 weeks. Y1194 was grown in two different fields (5801 and 5907).

| | field no. | plant no. | average | shelflife on the plant in weeks per fruit | | | | | |
|---|---|---|---|---|---|---|---|---|---|
| Y1194 | 5801 | 1 | 6 | 5 | 6 | 6 | 7 | | |
| | | 2 | 7.6 | 6 | 7 | 8 | 8 | 9 | |
| | | 3 | 6.5 | 5 | 6 | 6 | 7 | 7 | 8 |
| | | 4 | 6.8 | 6 | 6 | 6 | 8 | 8 | |
| | 5907 | 1 | 7.5 | 5 | 8 | 8 | 8 | 8 | 8 |
| | | 2 | 7.2 | 6 | 7 | 7 | 8 | 8 | |
| | | 3 | 7 | 4 | 7 | 7 | 6 | 8 | 7 | 8 | 9 |
| | | 4 | 7.4 | 5 | 6 | 8 | 9 | 9 | |
| Sprinter (control) | 5909 | 1 | 4.1 | 3 | 5 | 3 | 4 | 4 | 5 | 5 |
| | | 2 | 4.5 | 5 | 5 | 4 | 4 | | |
| | | 3 | 4.5 | 4 | 4 | 5 | 5 | | |
| | | 4 | 4.7 | 4 | 4 | 5 | 5 | 5 | 5 |
| F3 Y1194 | 5865 | 1 | 5.6 | 4 | 5 | 4 | 5 | 5 | 8 | 8 |
| | | 2 | 4.4 | 4 | 4 | 5 | 4 | 5 | |
| | | 3 | 4.3 | 4 | 4 | 5 | | | |
| | | 4 | 4.3 | 4 | 4 | 3 | 3 | 5 | 4 | 6 | 5 |
| | | 5 | 5.7 | 5 | 5 | 7 | | | |
| | | 6 | 5.0 | 4 | 5 | 4 | 5 | 7 | |
| | 5866 | 1 | 5.6 | 5 | 4 | 6 | 6 | 7 | |
| | | 2 | 5.6 | 5 | 4 | 5 | 6 | 5 | 7 | 7 |
| | | 3 | 7.7 | 7 | 7 | 9 | | | |
| | | 4 | 7.0 | 7 | 7 | | | | |
| | | 5 | 6.2 | 5 | 5 | 6 | 6 | 8 | 7 |
| | | 6 | 8.2 | 7 | 7 | 9 | 9 | 9 | 8 |
| | 5867 | 1 | 7.9 | 6 | 5 | 6 | 9 | 11 | 9 | 9 |
| | | 2 | 6.0 | 5 | 7 | | | | |
| | | 3 | 8.0 | 8 | | | | | |
| | | 4 | 8.3 | 6 | 8 | 10 | 8 | 8 | 10 |
| | | 5 | 8.5 | 7 | 8 | 9 | 9 | 9 | 9 |
| | 5868 | 1 | 8.2 | 8 | 7 | 8 | 7 | 9 | 10 |
| | | 2 | 8.7 | 8 | 9 | 9 | 8 | 9 | 9 |
| | | 3 | 6.3 | 6 | 6 | 6 | 6 | 6 | 6 | 8 |
| | | 4 | 7.4 | 5 | 6 | 8 | 9 | 8 | 8 | 8 |
| | | 5 | 5.8 | 6 | 6 | 6 | 5 | 4 | 6 | 7 |
| | | 6 | 8.8 | 7 | 11 | 8 | 9 | | |
| | 5869 | 1 | 8.3 | 7 | 8 | 9 | 9 | | |
| | | 2 | 8.8 | 8 | 9 | 9 | 9 | 9 | |
| | | 3 | 7.5 | 7 | 6 | 8 | 8 | 8 | 8 |
| | | 4 | 7.4 | 6 | 8 | 7 | 8 | 8 | |

Example 14

Breeding History of Pepper Line ZORO.27.42.7:DH1004

Line ZORO.27.42.7:DH1004 was obtained by crossing a jalapeno line derived from jalapeno Mexican landrace variety 87C307 (received from New Mexico State University) 3 times with a red or yellow blocky lines. The jalapeno line used in the cross is a parent of commercial jalapeno variety Firenza (Syngenta Seeds), which produces a fruit harvested at the green stage before full coloring. A F1 plant (Jalapeno× Blocky) was crossed with a F2 plant derived from 2 yellow blocky lines. A resulting progeny plant was crossed to the male parent of ROXY (Syngenta Seeds) and the resulting progeny was self-pollinated four times.

Example 15

Extended Storability on the Plant of Pepper Fruits of Lines

ZORO.27.42.7:DH 1004 (ZORO 1004) and ZORO.27.42.7:DH1005 (ZORO 1005)

Lines ZORO 1004 and ZORO 1005 are dihaploid lines derived from the same original line. Plants were grown as described above in example 11. The first fruit setting was observed 9 weeks after sowing. The first fruit with full coloring on the plant was observed 16 weeks after sowing. Setted fruits of 1-2 cm in size were labelled at the beginning of each week and the week number noted.

Only fruits considered marketable at the time of full coloring where followed and scored. It is noted that of fruitrot but were included in the study and in the table below.

Marketability of Fruits Kept on the Plant

Table 9 shows the percentage of marketable fruits in weeks after full coloring on the plant for Lines ZORO 1004 and ZORO 1005. Marketable fruits were judged for their appearance and on how they would appeal to consumers. In particular, when lack of firmness, wilting, climacteric degradation, or lack of brightness as described herein was observed, the fruits were judged as not marketable.

After full coloring each fruit was checked weekly. The following number of plants and fruits were evaluated and are reported in Table 7:

ZORO1004: 4 plants, 22 fruits; ZORO1005: 4 plants, 25 fruits.

TABLE 9

| | Weeks after full coloring on the plant | | | | | | |
|---|---|---|---|---|---|---|---|
| | 2 | 3 | 4 | 5 | 6 | 7 | 8 |
| ZORO1004 | 100 | 100 | 100 | 100 | 86 | 68 | 23 |
| ZORO1005 | 100 | 100 | 100 | 100 | 84 | 68 | 32 |

Table 9 shows for example that about 100% of fruits of lines ZORO 1004 and ZORO 1005 are still marketable 5 weeks after full coloring on the plant, and that about 85% of the fruits of lines ZORO 1004 and ZORO 1005 are still marketable 6 weeks after full coloring on the plant.

TABLE 10

The data in Table 10 shows the raw data for all fruits used in Table 9, and as described in Table 7.

| | field no. | plant no. | average | shelflife on the plant in weeks per fruit | | | | | | |
|---|---|---|---|---|---|---|---|---|---|---|
| ZORO 1004 | 5813 | 1 | 7.5 | 7 | 7 | 7 | 8 | 8 | 8 | |
| | | 2 | 6.8 | 6 | 6 | 6 | 7 | 8 | 8 | |
| | | 3 | 8.8 | 8 | 10 | 8 | 9 | | | |
| | | 4 | 8.7 | 8 | 9 | 9 | 10 | 8 | 8 | |
| ZORO 1005 | 5814 | 1 | 6.8 | 6 | 6 | 7 | 7 | 8 | | |
| | | 2 | 7.3 | 6 | 6 | 7 | 9 | 8 | 8 | 7 |
| | | 3 | 8.2 | 8 | 8 | 8 | 9 | 8 | 8 | |
| | | 4 | 9 | 9 | 9 | 9 | 8 | 10 | 9 | 9 |

Example 16

Extended Storability on the Plant of Pepper Fruits of Progeny of the Male Parent of Y1194 and the Precursor of Line ZORO.27.42.7:DH1004

Plants were grown as described above in Example 11. The male parent of Y1194 was crossed with the precursor of line ZORO.27.42.7:DH1004 before the dihaploidisation process. Plants in a particular group (5870-5885) are F3 plants originating from the same F1 plant from the cross.

Only fruits considered marketable at the time of full coloring where followed and scored. In field 5873, 1 plant with fruitrot was observed.

Marketability of Fruits Kept on the Plant

Table 11 shows the percentage of marketable fruits in weeks after full coloring on the plant. Marketable fruits were judged for their appearance and on how they would appeal to consumers. In particular, when lack of firmness, wilting, climacteric degradation, or lack of brightness as described, the fruits were judged as not marketable. After full coloring each fruit was checked weekly visually. The following number of plants and fruits were evaluated and are reported in Table 11:

5870: 4 plants, 27 fruits; 5871: 4 plants, 16 fruits 5872: 6 plants, 46 fruits; 5873: 6 plants, 45 fruits; 5874: 6 plants, 38 fruits; 5875: 5 plants, 44 fruits; 5876: 6 plants, 36 fruits; 5877: 3 plants, 22 fruits; 5878: 4 plants, 25 fruits; 5879: 6 plants, 42 fruits; 5880: 6 plants, 22 fruits; 5881: 4 plants, 21 fruits; 5882: 6 plants, 32 fruits; 5883: 6 plants, 31 fruits; 5884: 3 plants, 13 fruits; 5885: 6 plants, 34 fruits.

TABLE 11

| | Weeks after full coloring on the plant | | | | | | |
|---|---|---|---|---|---|---|---|
| | 2 | 3 | 4 | 5 | 6 | 7 | 8 |
| 5870 | 100 | 100 | 100 | 100 | 100 | 89 | 70 |
| 5871 | 100 | 100 | 100 | 94 | 88 | 75 | 75 |
| 5872 | 100 | 100 | 98 | 91 | 76 | 61 | 41 |
| 5873 | 100 | 100 | 100 | 93 | 78 | 60 | 29 |
| 5874 | 100 | 100 | 89 | 87 | 68 | 42 | 26 |
| 5875 | 100 | 100 | 98 | 82 | 70 | 52 | 32 |
| 5876 | 100 | 97 | 81 | 64 | 47 | 30 | 8 |
| 5877 | 100 | 95 | 77 | 36 | 27 | 5 | 5 |
| 5878 | 100 | 96 | 88 | 80 | 64 | 40 | 32 |
| 5879 | 98 | 93 | 50 | 21 | 12 | 0 | 0 |
| 5880 | 100 | 100 | 95 | 95 | 91 | 91 | 86 |
| 5881 | 100 | 100 | 100 | 95 | 90 | 81 | 71 |
| 5882 | 100 | 100 | 100 | 97 | 97 | 84 | 69 |
| 5883 | 100 | 100 | 100 | 97 | 94 | 84 | 74 |
| 5884 | 100 | 100 | 100 | 100 | 92 | 77 | 38 |
| 5885 | 100 | 100 | 97 | 88 | 82 | 79 | 47 |

Table 11 shows for example that about 100% of fruits of plants in group 5870 are still marketable 6 weeks after full coloring on the plant, and that about 90% of the fruits of plants in group 5870 are still marketable 7 weeks after full coloring on the plant.

TABLE 12

The data in Table 12 shows the raw data for all fruits used in Table 11, and as described in Table 7.

| field no. | plant no. | average | | | | shelflife on the plant in weeks per fruit | | | | | | |
|---|---|---|---|---|---|---|---|---|---|---|---|---|
| 5870 | 1 | 8.7 | 8 | 8 | 8 | 10 | 9 | 9 | | | | |
| | 2 | 9.0 | 8 | 8 | 7 | 12 | 9 | 9 | 9 | 10 | | |
| | 3 | 10.8 | 12 | 11 | 11 | 11 | 10 | 10 | | | | |
| | 4 | 9.1 | 7 | 7 | 11 | 11 | 10 | 9 | 9 | | | |
| 5871 | 1 | 9.0 | 9 | 9 | 9 | | | | | | | |
| | 2 | 6.5 | 6 | 5 | | | | | | | | |
| | 3 | 10.2 | 10 | 10 | 11 | 10 | 10 | | | | | |
| | 4 | 9.0 | 7 | 7 | 10 | 10 | 10 | 10 | | | | |
| 5872 | 1 | 9.3 | 4 | 8 | 10 | 9 | 7 | 11 | 11 | 11 | 11 | |
| | 2 | 5.7 | 6 | 6 | 5 | 6 | 6 | 5 | | | | |
| | 3 | 9.1 | 8 | 8 | 7 | 11 | 10 | 10 | 10 | | | |
| | 4 | 8.1 | 6 | 8 | 7 | 9 | 8 | 8 | 8 | 11 | | |
| | 5 | 9.3 | 8 | 10 | 10 | 10 | 9 | 9 | 9 | | | |
| | 6 | 6.6 | 6 | 5 | 7 | 7 | 7 | 8 | 6 | 7 | | |
| 5873 | 1 | 6.9 | 5 | 6 | 8 | 8 | 7 | 7 | 7 | 6 | 7 | 8 |
| | 2 | 7.9 | 6 | 7 | 8 | 8 | 8 | 7 | 10 | 9 | | |
| | 3 | 7.4 | 5 | 7 | 5 | 8 | 8 | 8 | 9 | 8 | 8 | |
| | 4 | 8.4 | 6 | 9 | 9 | 9 | | | | | | |
| | 5 | 8.4 | 6 | 6 | 7 | 10 | 10 | 9 | 9 | 10 | | |
| | 6 | 7.8 | 6 | 9 | 8 | 8 | | | | | | |
| 5874 | 1 | 5.3 | 5 | 4 | 4 | 6 | 6 | 7 | | | | |
| | 2 | 9.2 | 9 | 10 | 9 | 9 | 9 | 9 | | | | |
| | 3 | 6.2 | 4 | 7 | 6 | 6 | 6 | 6 | 7 | 7 | 7 | |
| | 4 | 7.8 | 7 | 8 | 8 | 8 | | | | | | |
| | 5 | 7.6 | 6 | 7 | 7 | 9 | 9 | | | | | |
| | 6 | 7.6 | 4 | 8 | 7 | 10 | 8 | 8 | 7 | 9 | | |
| 5875 | 1 | 8.0 | 8 | 8 | | | | | | | | |
| | 2 | 8.6 | 5 | 7 | 7 | 9 | 11 | 10 | 10 | 8 | 9 | 9 | 9 |
| | 3 | 7.3 | 5 | 7 | 6 | 9 | 7 | 7 | 7 | 7 | 9 | 9 |
| | 4 | 6.9 | 6 | 5 | 5 | 4 | 8 | 9 | 9 | 9 | | |
| | 5 | 6.6 | 5 | 5 | 6 | 6 | 6 | 5 | 8 | 8 | 8 | 8 | 8 |
| 5876 | 1 | 6.5 | 5 | 5 | 6 | 5 | 7 | 8 | 8 | 8 | | |
| | 2 | 4.5 | 3 | 4 | 4 | 4 | 4 | 8 | | | | |
| | 3 | 6.8 | 7 | 7 | 4 | 6 | 6 | 8 | 8 | 8 | | |
| | 4 | 6.3 | 5 | 7 | 4 | 5 | 5 | 7 | 9 | 8 | | |
| | 5 | 7.4 | 7 | 6 | 6 | 9 | 9 | | | | | |
| | 6 | 6.0 | 6 | | | | | | | | | |
| 5877 | 1 | 5.4 | 5 | 4 | 5 | 4 | 5 | 7 | 5 | 5 | 7 | 7 |
| | 2 | 6.5 | 3 | 6 | 7 | 7 | 5 | 11 | | | | |
| | 3 | 4.8 | 5 | 5 | 5 | 4 | 6 | 4 | | | | |
| 5878 | 1 | 6.2 | 4 | 6 | 5 | 7 | 9 | | | | | |
| | 2 | 5.6 | 5 | 7 | 3 | 6 | 7 | | | | | |
| | 3 | 6.2 | 4 | 7 | 6 | 6 | 8 | | | | | |
| | 4 | 9.2 | 7 | 9 | 10 | 11 | 9 | | | | | |
| | 5 | 8.8 | 9 | 11 | 7 | 9 | 8 | | | | | |
| 5879 | 1 | 4.5 | 4 | 4 | 4 | 2 | 4 | 5 | 7 | 6 | | |
| | 2 | 4.3 | 4 | 4 | 4 | 4 | 4 | 6 | | | | |
| | 3 | 4.2 | 4 | 4 | 3 | 4 | 4 | 6 | | | | |
| | 4 | 5.0 | 4 | 4 | 4 | 5 | 5 | 5 | 5 | 7 | 6 | |
| | 5 | 5.4 | 4 | 5 | 5 | 5 | 5 | 5 | 7 | 7 | | |
| | 6 | 4.8 | 4 | 3 | 5 | 5 | 7 | | | | | |
| 5880 | 1 | 9.8 | 10 | 10 | 10 | 9 | | | | | | |
| | 2 | 8.6 | 6 | 10 | 9 | 9 | 9 | | | | | |
| | 3 | 4.0 | 4 | | | | | | | | | |
| | 4 | 10.5 | 11 | 11 | 11 | 9 | | | | | | |
| | 5 | 9.3 | 10 | 10 | 9 | 8 | | | | | | |
| | 6 | 9.5 | 10 | 10 | 9 | 9 | | | | | | |
| 5881 | 1 | 9.0 | 10 | 9 | 9 | 8 | 9 | | | | | |
| | 2 | 8.7 | 7 | 5 | 8 | 11 | 11 | 10 | | | | |
| | 3 | 7.3 | 7 | 6 | 9 | | | | | | | |
| | 4 | 10.2 | 10 | 10 | 10 | 10 | 11 | | | | | |
| | 5 | 10.5 | 10 | 11 | | | | | | | | |
| 5882 | 1 | 8.4 | 7 | 7 | 7 | 9 | 9 | 10 | 10 | | | |
| | 2 | 8.9 | 8 | 8 | 9 | 9 | 11 | 9 | 8 | | | |
| | 3 | 8.3 | 8 | 7 | 10 | | | | | | | |
| | 4 | 9.6 | 9 | 11 | 9 | 9 | 10 | | | | | |
| | 5 | 9.4 | 8 | 9 | 10 | 10 | 10 | | | | | |
| | 6 | 8.6 | 5 | 9 | 10 | 10 | 9 | | | | | |
| 5883 | 1 | 8.6 | 6 | 5 | 11 | 10 | 10 | 9 | 9 | | | |
| | 2 | 9.0 | 8 | 9 | 9 | 10 | | | | | | |
| | 3 | 8.3 | 7 | 7 | 10 | 9 | 9 | 8 | | | | |
| | 4 | 10.0 | 11 | 10 | 10 | 9 | | | | | | |

TABLE 12-continued

The data in Table 12 shows the raw data for all fruits used in Table 11, and as described in Table 7.

| field no. | plant no. | average | shelflife on the plant in weeks per fruit | | | | | | | |
|---|---|---|---|---|---|---|---|---|---|---|
| | 5 | 9.2 | 7 | 8 | 10 | 10 | 10 | 10 | | |
| | 6 | 9.8 | 11 | 10 | 9 | 9 | | | | |
| 5884 | 1 | 8.3 | 6 | 8 | 10 | 9 | | | | |
| | 2 | 8.0 | 8 | 8 | 7 | 9 | | | | |
| | 3 | 8.2 | 7 | 9 | 9 | 8 | 8 | | | |
| 5885 | 1 | 8.1 | 4 | 7 | 10 | 8 | 8 | 9 | 11 | |
| | 2 | 8.0 | 6 | 9 | 8 | 9 | | | | |
| | 3 | 7.3 | 5 | 6 | 9 | 9 | | | | |
| | 4 | 8.9 | 8 | 9 | 11 | 8 | 10 | 8 | 9 | 8 |
| | 5 | 7.2 | 5 | 5 | 8 | 8 | 9 | 8 | | |
| | 6 | 9.2 | 8 | 11 | 9 | 9 | 9 | | | |

Example 17

Extended Storability on the Plant of Pepper Fruits of Progeny of the Female Parent of Y1194 and the Precursor of Line ZORO.27.42.7:DH1004

Plants were grown as described above in Example 11. The female parent of Y1194 was crossed with the precursor of line ZORO.27.42.7:DH11004 before the dihaploidisation process. Plants in a particular group (5886-5897) are F3 plants originating from the same F1 plant from the cross.

The first fruit setting was observed 9 weeks after sowing. The first fruit with full coloring on the plant was observed 16 weeks after sowing. Setted fruits of 1-2 cm in size were labelled at the beginning of each week and the week number noted.

Only fruits considered marketable at the time of full coloring where followed and scored.

Marketability of Fruits Kept on the Plant

Table 13 shows the percentage of marketable fruits in weeks after full coloring on the plant. Marketable fruits were judged for their appearance and on how they would appeal to consumers. In particular, when lack of firmness, wilting, climacteric degradation, or lack of brightness as described herein was observed, the fruits were judged as not marketable. After full coloring each fruit was checked weekly visually. The following number of plants and fruits were evaluated and are reported in Table 13:

5886: 6 plants, 33 fruits; 5887: 6 plants, 58 fruits; 5888: 6 plants, 43 fruits; 5889: 6 plants, 59 fruits; 5890: 6 plants, 38 fruits; 5891: 6 plants, 39 fruits; 5892: 5 plants, 37 fruits; 5893: 5 plants, 38 fruits; 5894: 5 plants, 37 fruits; 5895: 4 plants, 25 fruits; 5896: 6 plants, 56 fruits; 5897: 5 plants, 20 fruits.

TABLE 13

| | Weeks after full coloring on the plant | | | | | | |
|---|---|---|---|---|---|---|---|
| | 2 | 3 | 4 | 5 | 6 | 7 | 8 |
| 5886 | 100 | 100 | 100 | 100 | 97 | 91 | 82 |
| 5887 | 100 | 90 | 58 | 34 | 12 | 2 | 0 |
| 5888 | 100 | 95 | 60 | 16 | 7 | 5 | 0 |
| 5889 | 100 | 90 | 44 | 7 | 0 | 0 | 0 |
| 5890 | 100 | 100 | 100 | 100 | 89 | 63 | 58 |
| 5891 | 95 | 79 | 41 | 28 | 23 | 18 | 5 |
| 5892 | 100 | 100 | 100 | 86 | 68 | 59 | 38 |
| 5893 | 100 | 100 | 97 | 95 | 79 | 63 | 42 |
| 5894 | 100 | 100 | 100 | 100 | 92 | 92 | 65 |
| 5895 | 96 | 76 | 48 | 32 | 16 | 12 | 0 |
| 5896 | 100 | 95 | 45 | 11 | 5 | 2 | 0 |
| 5897 | 100 | 100 | 85 | 55 | 50 | 20 | 15 |

Table 13 shows for example that about 100% of fruits of plants in group 5886 are still marketable 6 weeks after full coloring on the plant, and that about 90% of the fruits of plants in group 5870 are still marketable 7 weeks after full coloring on the plant.

TABLE 14

| field no. | plant no. | average | shelflife on the plant in weeks per fruit | | | | | | | | | |
|---|---|---|---|---|---|---|---|---|---|---|---|---|
| 5886 | 1 | 9.1 | 7 | 8 | 11 | 10 | 10 | 9 | 9 | | | |
| | 2 | 9.3 | 6 | 8 | 11 | 11 | 10 | 10 | | | | |
| | 3 | 10.0 | 7 | 11 | 11 | 11 | 10 | | | | | |
| | 4 | 9.7 | 9 | 8 | 11 | 11 | 10 | 9 | | | | |
| | 5 | 10.6 | 11 | 11 | 11 | 10 | 10 | | | | | |
| | 6 | 11.0 | 12 | 11 | 10 | 11 | | | | | | |
| 5887 | 1 | 4.3 | 5 | 3 | 6 | 4 | 4 | 3 | 4 | 5 | 5 | |
| | 2 | 4.9 | 6 | 6 | 6 | 6 | 3 | 4 | 3 | 4 | 6 | 6 | 4 | 5 |
| | 3 | 4.4 | 6 | 4 | 3 | 5 | 5 | 4 | 3 | 5 | 5 | |
| | 4 | 6.2 | 6 | 5 | 5 | 5 | 8 | 7 | 7 | 7 | 6 | |
| | 5 | 5.2 | 6 | 5 | 5 | 5 | 5 | 6 | 5 | 5 | 5 | |
| | 6 | 5.7 | 7 | 5 | 5 | 6 | 5 | 5 | 5 | 5 | 7 | 7 |

TABLE 14-continued

| field no. | plant no. | average | shelflife on the plant in weeks per fruit | | | | | | | | | |
|---|---|---|---|---|---|---|---|---|---|---|---|---|
| 5888 | 1 | 4.0 | 4 | | | | | | | | | |
| | 2 | 4.5 | 4 | 4 | 4 | 3 | 4 | 5 | 4 | 6 | 6 | 5 | 5 |
| | 3 | 4.4 | 5 | 4 | 4 | 4 | 4 | 5 | 4 | 5 | 5 | | |
| | 4 | 5.3 | 4 | 4 | 5 | 8 | | | | | | | |
| | 5 | 5.2 | 5 | 5 | 5 | 5 | 4 | 6 | 5 | 4 | 5 | 7 | |
| | 6 | 5.3 | 5 | 6 | 5 | 3 | 5 | 5 | 5 | 8 | | | |
| 5889 | 1 | 4.3 | 5 | 5 | 4 | 5 | 3 | 3 | 5 | 4 | | | |
| | 2 | 4.8 | 4 | 4 | 3 | 5 | 6 | 6 | 4 | 5 | 5 | 6 | 5 |
| | 3 | 4.3 | 5 | 4 | 3 | 5 | 4 | 3 | 5 | 5 | | | |
| | 4 | 4.2 | 4 | 4 | 4 | 4 | 4 | 4 | 5 | 4 | 4 | 5 | |
| | 5 | 4.5 | 4 | 4 | 3 | 5 | 5 | 4 | 4 | 6 | 5 | 4 | 5 | 5 |
| | 6 | 4.3 | 4 | 4 | 4 | 4 | 4 | 5 | 5 | 5 | | | |
| 5890 | 1 | 7.9 | 6 | 6 | 7 | 7 | 11 | 9 | 7 | 10 | 8 | | |
| | 2 | 7.2 | 6 | 7 | 7 | 7 | 7 | 9 | | | | | |
| | 3 | 9.0 | 6 | 11 | 11 | 9 | 9 | 9 | 8 | | | | |
| | 4 | 8.5 | 7 | 9 | 9 | 9 | | | | | | | |
| | 5 | 9.7 | 7 | 7 | 12 | 12 | 10 | 10 | 10 | | | | |
| | 6 | 10.2 | 12 | 9 | 10 | 10 | 10 | | | | | | |
| 5891 | 1 | 3.9 | 4 | 4 | 3 | 3 | 4 | 4 | 5 | | | | |
| | 2 | 4.5 | 4 | 4 | 5 | 4 | 4 | 6 | | | | | |
| | 3 | 4.0 | 4 | 4 | 4 | 3 | 5 | | | | | | |
| | 4 | 8.1 | 6 | 9 | 8 | 8 | 8 | 7 | 11 | 8 | | | |
| | 5 | 2.8 | 4 | 3 | 2 | 2 | 3 | 3 | | | | | |
| | 6 | 5.3 | 4 | 4 | 5 | 5 | 4 | 8 | 7 | | | | |
| 5892 | 1 | 9.3 | 6 | 8 | 11 | 11 | 10 | 10 | 9 | 9 | 8 | 11 | |
| | 2 | 6.4 | 5 | 6 | 5 | 6 | 7 | 8 | 8 | | | | |
| | 3 | 8.3 | 8 | 8 | 8 | 7 | 9 | 9 | 9 | | | | |
| | 4 | 5.8 | 6 | 6 | 5 | 5 | 6 | 6 | 5 | 7 | | | |
| | 5 | 10.2 | 10 | 10 | 11 | 12 | 8 | | | | | | |
| 5893 | 1 | 6.0 | 6 | 6 | 4 | 8 | | | | | | | |
| | 2 | 9.1 | 9 | 9 | 9 | 8 | 11 | 10 | 8 | 8 | 10 | 9 | |
| | 3 | 6.3 | 6 | 6 | 6 | 7 | 5 | 7 | 7 | | | | |
| | 4 | 9.4 | 9 | 8 | 11 | 7 | 10 | 10 | 11 | | | | |
| | 5 | 8.0 | 6 | 7 | 8 | 8 | 9 | 8 | 7 | 8 | 10 | 9 | |
| 5894 | 1 | 8.9 | 9 | 9 | 8 | 9 | 9 | 9 | 10 | 8 | | | |
| | 2 | 7.6 | 6 | 6 | 6 | 8 | 10 | 8 | 8 | 8 | 8 | | |
| | 3 | 10.2 | 11 | 11 | 10 | 9 | 10 | 10 | | | | | |
| | 4 | 9.3 | 11 | 10 | 10 | 9 | 8 | 8 | | | | | |
| | 5 | 10.1 | 8 | 10 | 10 | 11 | 11 | 10 | 11 | 10 | | | |
| 5895 | 1 | 3.0 | 3 | 3 | 4 | 2 | 3 | 3 | | | | | |
| | 2 | 4.1 | 4 | 4 | 5 | 5 | 3 | 4 | 4 | | | | |
| | 3 | 5.5 | 4 | 5 | 6 | 4 | 6 | 6 | 7 | | | | |
| | 4 | 6.7 | 5 | 5 | 6 | 8 | 8 | 8 | | | | | |
| 5896 | 1 | 4.2 | 4 | 4 | 5 | 4 | 4 | 4 | | | | | |
| | 2 | 5.4 | 5 | 5 | 5 | 3 | 6 | 5 | 6 | 8 | | | |
| | 3 | 4.1 | 5 | 4 | 4 | 4 | 5 | 4 | 3 | 4 | | | |
| | 4 | 4.2 | 5 | 4 | 4 | 5 | 4 | 4 | 5 | 4 | 4 | 3 | 4 |
| | 5 | 4.8 | 4 | 6 | 5 | 5 | 4 | 4 | 4 | 5 | 7 | | |
| | 6 | 4.9 | 5 | 5 | 5 | 5 | 5 | 4 | 4 | 4 | 4 | 5 | 7 |
| 5897 | 1 | 5.3 | 7 | 4 | 5 | | | | | | | | |
| | 2 | 5.5 | 6 | 5 | | | | | | | | | |
| | 3 | 6.6 | 4 | 5 | 7 | 8 | 9 | | | | | | |
| | 4 | 7.5 | 5 | 7 | 9 | 9 | | | | | | | |
| | 5 | 5.8 | 5 | 5 | 4 | 7 | 7 | 7 | | | | | |

What is claimed is:

1. A seed of *Capsicum* hybrid Y1194, wherein a representative sample of said seed has been deposited under Accession No. NCIMB 41187, or a seed of *Capsicum* line ZORO.27.42.7:DH1004, wherein a representative sample of said seed has been deposited under Accession No. NCIMB 41241.

2. A plant, or a part thereof, produced from the seed of claim 1.

3. A tissue culture of cells produced from the plant of claim 2, wherein said cells of the tissue culture are produced from a plant part selected from the group consisting of embryo, meristematic cell, leaf, cotyledon, hypocotyl, stem, root, root tip, pistil, anther, flower, seed and pollen.

4. A protoplast produced from the plant of claim 2.

5. A protoplast produced from the tissue culture of claim 3.

6. A *Capsicum* plant regenerated from the tissue culture of claim 3, wherein the plant has all of the morphological and physiological characteristics of hybrid Y1194, representative seed of which is deposited under Accession No. NCIMB 41187, or line ZORO.27.42.7:DH1004, representative seed of which is deposited under Accession No. NCIMB 41241.

7. The plant according to claim 2, wherein said plant is a *Capsicum annuum* plant.

8. The plant according to claim 2, wherein a fruit of said plant is yellow, orange, ivory or red.

9. A method for producing a *Capsicum* seed comprising crossing two parent *Capsicum* plants and harvesting the resultant *Capsicum* seed, wherein at least one of said parent *Capsicum* plants is the *Capsicum* plant of claim 2.

10. The method of claim 9 comprising two or more generations of back crossing to one of said parent *Capsicum* plants.

* * * * *